United States Patent
Mason

(10) Patent No.: US 11,116,526 B2
(45) Date of Patent: Sep. 14, 2021

(54) INTRAMEDULLARY BASED AND OMNI-POSITIONABLE CUTTING GUIDE INSTRUMENTATION FOR FEMORAL EPIPHYSIS RESECTION FOR KNEE PROSTHESIS PLACEMENT AND A METHOD OF OPERATION THEREOF

(71) Applicant: Michael Mason, Boston, MA (US)

(72) Inventor: Michael Mason, Boston, MA (US)

( * ) Notice: Subject to any disclaimer, the term of this patent is extended or adjusted under 35 U.S.C. 154(b) by 608 days.

(21) Appl. No.: 15/999,758

(22) PCT Filed: Feb. 17, 2017

(86) PCT No.: PCT/AU2017/050140
§ 371 (c)(1),
(2) Date: Aug. 20, 2018

(87) PCT Pub. No.: WO2017/139850
PCT Pub. Date: Aug. 24, 2017

(65) Prior Publication Data
US 2020/0237384 A1    Jul. 30, 2020

(30) Foreign Application Priority Data
Feb. 18, 2016   (AU) .................. 2016900567

(51) Int. Cl.
*A61B 17/58* (2006.01)
*A61B 17/60* (2006.01)
(Continued)

(52) U.S. Cl.
CPC .......... *A61B 17/1764* (2013.01); *A61B 17/72* (2013.01); *A61B 2017/564* (2013.01)

(58) Field of Classification Search
CPC combination set(s) only.
See application file for complete search history.

(56) References Cited

U.S. PATENT DOCUMENTS 5,662,656 A * 9/1997 White .................. A61B 17/155
                                                                606/86 R
6,013,081 A    1/2000 Burkinshaw et al.
(Continued)

FOREIGN PATENT DOCUMENTS

EP           0243109 B1    9/1993
WO       1996025114 A1    8/1996
(Continued)

OTHER PUBLICATIONS

International Search Report & Written Opinion dated May 26, 2017 from corresponding PCT Application No. PCT/AU2017/050140.
(Continued)

*Primary Examiner* — Sameh R Boles
(74) *Attorney, Agent, or Firm* — Innovation Capital Law Group, LLC; Vic Lin

(57) ABSTRACT

An intramedullary based & omni-positionable cutting guide instrumentation for femoral epiphysis resection for knee prosthesis placement comprising: an intramedullary placement guide (1,27) in a medullary cavity of a femoral epiphysis having an anterior/posterior adjustment mechanism (33); posterior rotational referencing sizing jig (8) for fastening to the anterior/posterior adjustment mechanism (33) and configured for referencing anterior (10) and posterior (11, 18) surfaces of the femoral epiphysis to adjust the anterior/posterior offset of the anterior/posterior adjustment mechanism (33); and a punch card (20) for subsequent fastening to the anterior/posterior adjustment mechanism (33) and comprising a plurality of position referencing apertures (21a-21d) for receipt of at least one locking pin (23) of a cutting block guide (5) to allow the anterior/posterior positioning of the cutting block guide (5) at a first position (e.g. FIG. 10) for making a first resection (e.g. 24)
(Continued)

and at a second position (e.g. FIG. 11) for the purposes of making a second resection (e.g. 37).

30 Claims, 37 Drawing Sheets

(51) Int. Cl.
*A61F 2/00* (2006.01)
*A61B 17/17* (2006.01)
*A61B 17/72* (2006.01)
*A61B 17/56* (2006.01)

(56) References Cited

U.S. PATENT DOCUMENTS

2007/0233138 A1 10/2007 Figueroa et al.
2008/0154270 A1 6/2008 Haines et al.

FOREIGN PATENT DOCUMENTS

| WO | 2009006741 A1 | 1/2009 |
| WO | 2012167016 A1 | 12/2012 |
| WO | 2014167104 A1 | 10/2014 |

OTHER PUBLICATIONS

International-type search report dated Feb. 1, 2017 from corresponding Australian Provisional Application No. 2016900567.

* cited by examiner

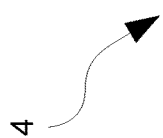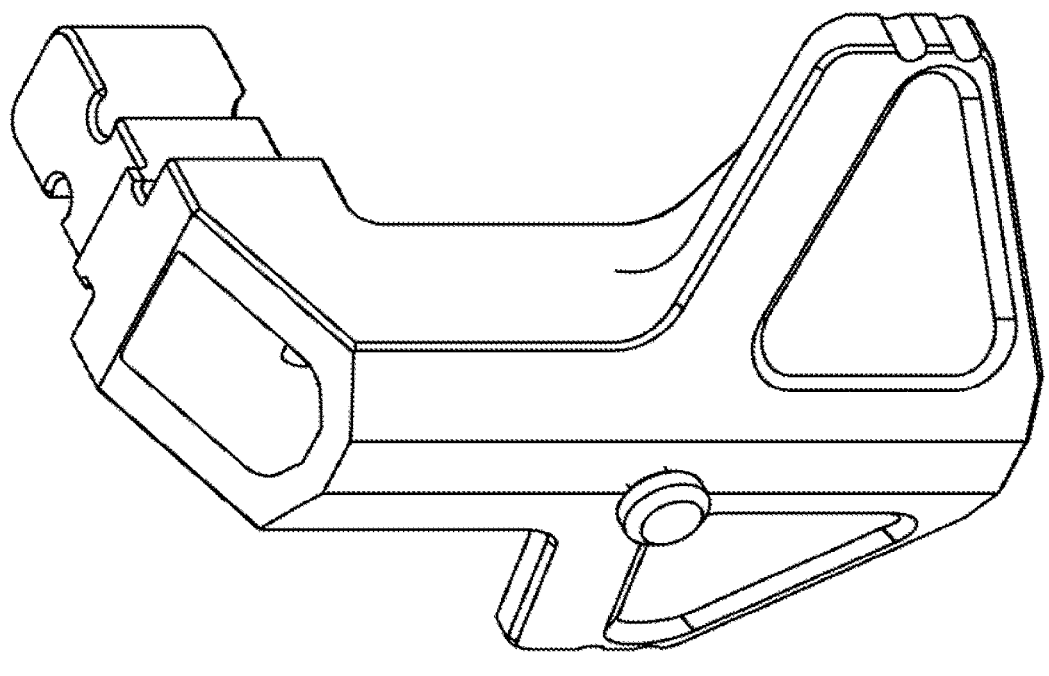
Figure 16

INTRAMEDULLARY BASED AND OMNI-POSITIONABLE CUTTING GUIDE INSTRUMENTATION FOR FEMORAL EPIPHYSIS RESECTION FOR KNEE PROSTHESIS PLACEMENT AND A METHOD OF OPERATION THEREOF

FIELD OF THE INVENTION

The present invention relates to knee prosthesis cutting guides and in particular, but not necessarily entirely, to intramedullary based and omni-positionable cutting guide instrumentation for femoral epiphysis resection for knee prosthesis placement and a method of operation thereof.

The invention has been developed primarily for use in/with knee prosthesis and will be described hereinafter with reference to this application. However, it will be appreciated that the invention is not limited to this particular field of use.

BACKGROUND OF THE INVENTION

The femoral epiphysis requires resection prior to placement of a knee prosthesis.

During surgery, cutting guides are utilised to guide the cutting tools for the purposes of making the various resections required. For example, five femoral resections may be required to prepare the femoral epiphysis for receipt of the knee prosthesis. The five femoral resections may comprise distal, posterior, posterior chamfer, anterior and anterior chamfer resections. A further proximal tibial resection may be required also for the tibial component of the knee prosthesis.

Existing cutting guide instrumentation comprises "4 in 1" cutting blocks able to make up to four of the femoral resections. However, a separate cutting block guide is therefore required to make the distal femoral and proximal tibial resections.

Furthermore, existing cutting blocks are size-specific and therefore differing sized and separate cutting blocks are required for each prosthesis size. For example, for a type of prosthesis having eight differing sizes, eight separate cutting blocks are required. Having multiple cutting blocks is expensive including for reasons that the cutting blocks are generally wire cut.

D1 (U.S. Pat. No. 5,662,656 A (WHITE) 2 Sep. 1997) discloses instrumentation for sizing the end of a distal femur, and resecting the distal femur.

However, the instrumentation of D1 can only be used to guide the distal and anterior femoral resections, and cannot be used to make the proximal tibia, anterior chamfer, posterior chamfer and posterior femur resections.

It would be advantageous to have cutting guide instrumentation able to make the five femoral and preferably also the distal tibial resection that reduces the number of cutting block guides, preferably to one.

The present invention seeks to provide an intramedullary based and omni-positionable cutting guide instrumentation for femoral epiphysis resection for knee prosthesis placement and a method of operation thereof, which will overcome or substantially ameliorate at least some of the deficiencies of the prior art, including those alluded to above and others, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

In the embodiments that follow, there will be described intramedullary based and omni-positionable cutting guide instrumentation for femoral epiphysis resection for knee prosthesis placement.

As alluded to above in the background section, and as shall become apparent from the ensuing description, the instrumentation dispenses with the requirement of multiple cutting blocks for differing sizing as is the case for prior art instrumentation. Specifically, the instrumentation disclosed herein comprises a single cutting block usable for performing the various femoral epiphysis resections for the purposes of knee prosthesis placement reducing the cost, complexity and maintenance of the instrumentation. The instrumentation also offers further advantages of the prior art.

According to a first aspect of the present invention, there is provided intramedullary based and omni-positionable cutting guide instrumentation for femoral epiphysis resection for knee prosthesis placement comprising: an intramedullary placement guide configured for insertion into a medullary cavity of a femoral epiphysis in use, the placement guide having an anterior/posterior adjustment mechanism; a posterior rotational referencing sizing jig for fastening to the anterior/posterior adjustment mechanism, the posterior rotational referencing sizing jig configured for referencing anterior and posterior surfaces of the femoral epiphysis so as to adjust the anterior/posterior offset of the anterior/posterior adjustment mechanism in use; a punch card for subsequent fastening to the anterior/posterior adjustment mechanism, the punch card comprising a plurality of position referencing apertures for receipt of at least one locking pin of a cutting block guide therein for the purposes of allowing the anterior/posterior positioning of the cutting block guide at a first position for the purposes of making a first resection and the anterior/posterior positioning of the cutting block guide at a second position for the purposes of making a second resection.

The plurality of apertures may comprise an aperture located for locating the cutting block guide for the purposes of making a posterior resection.

The cutting guide instrumentation may further comprise the cutting block guide and wherein the cutting block guide may comprise a posterior face configured for guiding the posterior resection.

The plurality of apertures may comprise an aperture located for locating the cutting block guide for the purposes of making a posterior chamfer resection.

The cutting guide instrumentation may further comprise the cutting block guide and wherein the cutting block guide may comprise a posterior chamfer slot configured for guiding the posterior resection.

The chamfer slot may be bifurcated in comprising respective lateral/medial accessible slot portions.

The plurality of apertures may comprise an aperture located for locating the cutting block guide for the purposes of making an anterior resection.

The cutting guide instrumentation may further comprise the cutting block guide and wherein the cutting block guide may comprise an anterior face configured for guiding the anterior resection.

The plurality of apertures may comprise an aperture located for locating the cutting block guide for the purposes of making an anterior chamfer resection.

The cutting guide instrumentation may further comprise the cutting block guide and wherein the cutting block guide may comprise a chamfer slot configured for guiding the posterior resection.

The chamfer slot may be bifurcated in comprising respective lateral/medial accessible slot portions.

The anterior/posterior adjustment mechanism may comprise a sliding member configured to travel along an anterior/posterior axis of the femoral epiphysis in use.

The sliding member may comprise placement pins configured for engaging the sizing jig.

The posterior rotational referencing sizing jig may comprise a size guide configured for estimating the sizing of the femoral epiphysis.

The posterior rotational referencing sizing jig may be configure for selectively engaging the placement guide at an anterior reference position and a posterior reference position.

The posterior rotational referencing sizing jig may comprise a spacer for internal rotation positioning the anterior/posterior adjustment mechanism.

The internal rotation may be substantially 3°.

The posterior rotational referencing sizing jig may be selectively positional for left knee and right knee application.

The placement guide may comprise a rod for insertion into the medullary cavity and a distal substantially orthogonal placement guide portion fastened to the rod.

The rod may be orientated at an offset from the perpendicular axis of the placement guide portion to accommodate femoral varus.

The varus may be substantially 6°.

The cutting guide instrumentation may further comprise a right angled bracket configured for selective engagement to the placement guide for the purposes of locating a cutting block guide for the purposes of making a distal resection.

The right angled may comprise laterally projecting condylar contacting flanges configured to control the positioning of the cutting block guide at a particular superior offset along the superior/inferior axis.

The superior offset may be approximately 9 mm.

The cutting guide instrumentation may further comprise the cutting block guide and wherein the cutting block guide may comprise a plurality of apertures for receiving bone fastening pins therethrough for fastening the cutting block guide to the with respect to the femoral epiphysis for allowing the removal of the right angled bracket.

The plurality of apertures are collocated for providing placement tolerance.

The placement tolerance may be lateral/medial placement tolerance.

The placement tolerance may be superior/inferior placement tolerance.

The placement tolerance may be approximately 2 mm.

According to another aspect, there is provided a method for femoral epiphysis resection comprising: placing an intramedullary placement guide; adjusting an adjustment mechanism of the placement guide using a sizing jig; locating a cutting block guide at a first position with reference to the adjustment mechanism; making a first resection; locating a cutting block guide at a second position with reference to the adjustment mechanism; and making a second resection.

According to another aspect, there is provided a cutting block guide for making resections, the cutting block guide being generally rectangular and defining top, anterior, posterior and bottom faces, wherein one or more of the top, anterior and posterior faces are configured for cutting instrument guidance for making distal femoral, anterior femoral and posterior femoral resections; and wherein the cutting block guide has a posterior chamfer slot configured for cutting instrument guidance for making a posterior chamfer femoral resection; and the cutting block guide has anterior chamfer slot configured for cutting instrument guidance for making an anterior chamfer femoral resection.

The posterior face may be configured for making the distal femoral resection when the posterior face may be orientated substantially orthogonal to the elongate axis a femur in use.

The top face may be configured for making the proximal tibial resection when the top face may be orientated substantially orthogonal to the elongate axis of a tibia in use.

The anterior face may be configured for making the anterior femoral resection.

The posterior face may be configured for making the posterior femoral resection.

The cutting block guide may be configured for making two or more of the anterior femoral, posterior femoral, posterior chamfer femoral and anterior chamfer femoral resections when the cutting block guide may be in two or more positions along an orthogonal axis substantially orthogonal to an elongate axis of a femur being resected in use.

The cutting block guide may be configured for making the posterior and posterior chamfer resections when the cutting block guide may be in a first position with reference to a femur.

The cutting block guide may be configured for making the anterior chamfer resection when the cutting block guide may be in a second position with reference to the femur.

The cutting block guide may be configured for making the anterior resection when the cutting block guide may be in a third position with reference to the femur.

Other aspects of the invention are also disclosed.

BRIEF DESCRIPTION OF THE DRAWINGS

Notwithstanding any other forms which may fall within the scope of the present invention, a preferred embodiment of the disclosure will now be described, by way of example only, with reference to the accompanying drawings in which:

FIGS. 14-20 show the cutting guide instrumentations in accordance with a further embodiment.

DESCRIPTION OF EMBODIMENTS

Figure 1:
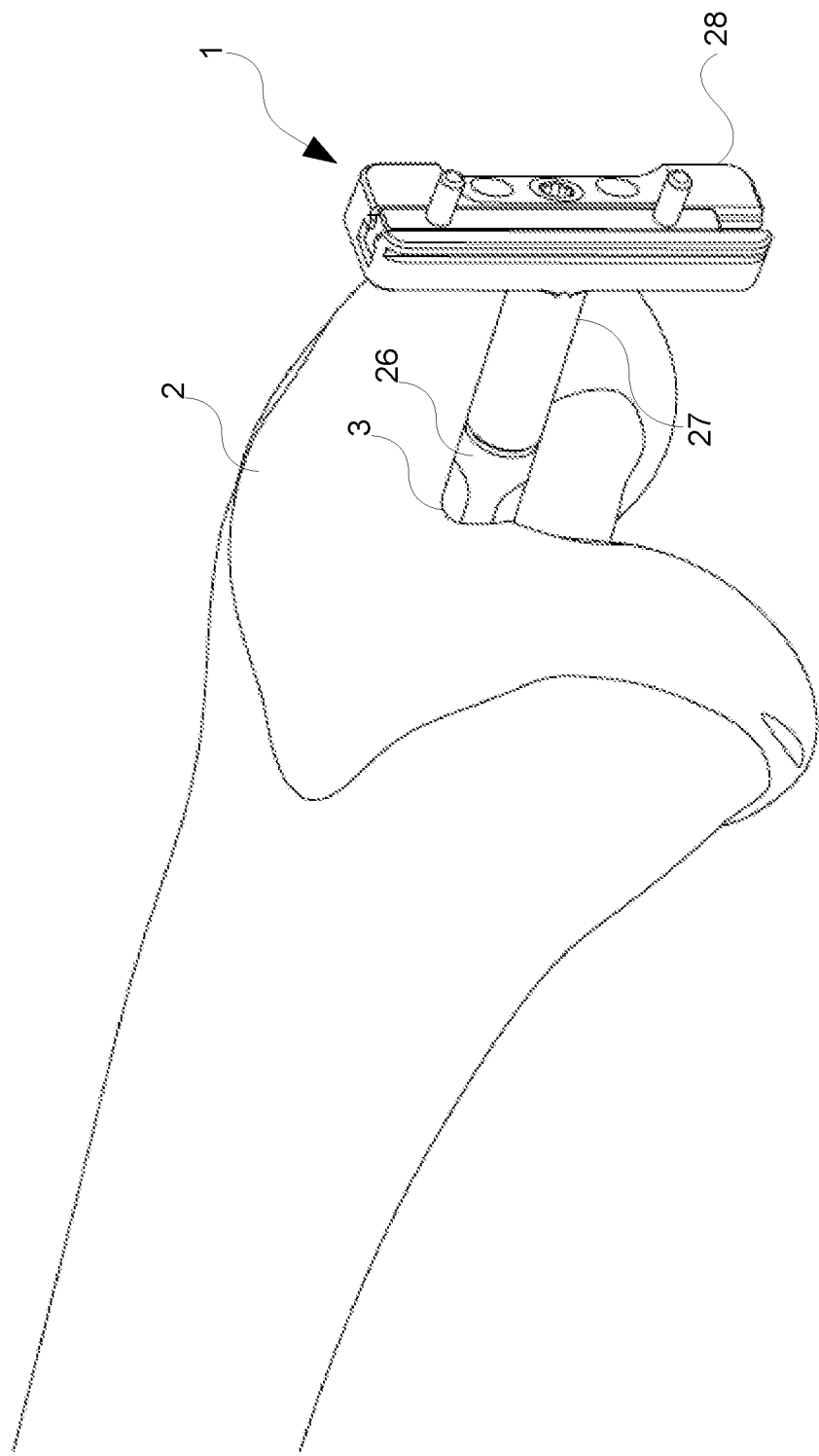
FIG. 1 shows an intramedullary placement guide of the instrument eight and being inserted into the medullary canal through an aperture of the femoral epiphysis.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure.

Before the structures, systems and associated methods relating to the intramedullary based and omni-positionable cutting guide instrumentation for femoral epiphysis resection for knee prosthesis placement and a method of operation thereof are disclosed and described, it is to be understood that this disclosure is not limited to the particular configurations, process steps, and materials disclosed herein as such may vary somewhat. It is also to be understood that the terminology employed herein is used for the purpose of describing particular embodiments only and is not intended to be limiting since the scope of the disclosure will be limited only by the claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterised by," and grammatical equivalents thereof are inclusive or open-ended terms that do not exclude additional, unrecited elements or method steps.

It should be noted in the following description that like or the same reference numerals in different embodiments denote the same or similar features.

Turning now to FIG. 1, there is shown the femoral epiphysis 2 being readied for resection for knee prosthesis placement.

In the figure, an intramedullary placement guide 1 is inserted into the medullary cavity of the femur. Specifically, a canal 3 is drilled through the distal end of the epiphysis 2 and into the medullary cavity. As can be seen, the placement guide 1 comprises a rod 27 for insertion into the aperture 3 and an orthogonal distal guide portion 28 as will be described in further detail below.

In an embodiment, the rod 27 may terminate in a bone penetrating tip 26 to aid the insertion thereof.

In a preferred embodiment, the rod is offset at substantially 6° from the perpendicular axis of the distal guide portion 28 to account for femoral varus such that the distal guide portion is orientated correctly.

Figure 2:
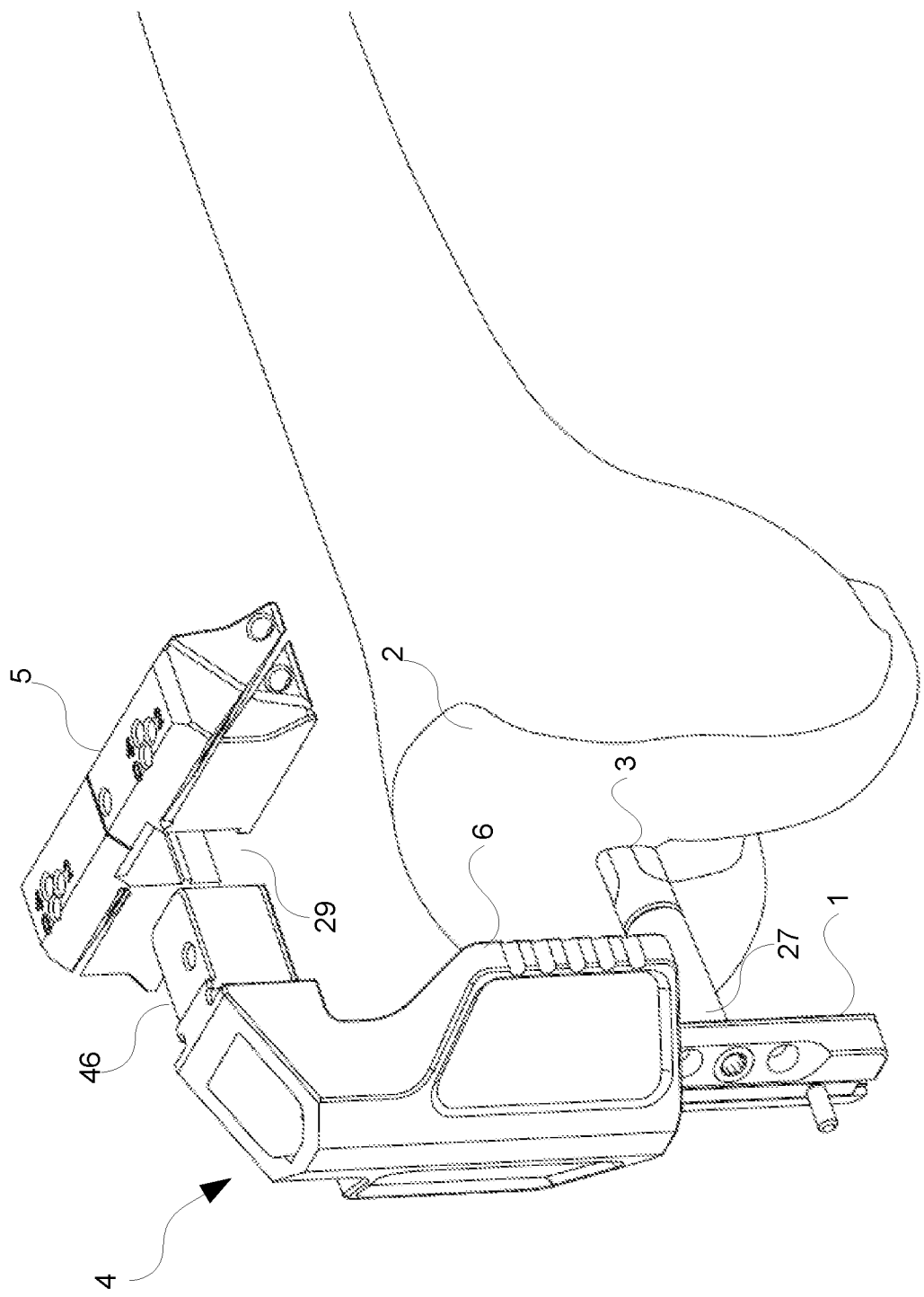
FIG. 2 shows a right angled bracket being fastened to the placement guide for the purposes of locating a cutting block for making the distal resection.

Now, for the purposes of making the distal resection, and turning now to FIG. 2, a right angled distal femoral referencing guide 4 is slidably engaged to the placement guide 1. The distal femoral referencing guide 4 is utilised for the purposes of placing a cutting block guide 5 for the purposes of making the distal resection.

Specifically, as can be seen, the distal femoral referencing guide 4 comprises laterally projecting condylar contacting flanges 6 such that the depth of placement of the cutting block guide 5 is with reference to the condylar distal aspect apogees. In this regard, the rod 27 is inserted into the aperture 3 until such time that the condylar contacting flanges 6 make contact with the inferior condylar apogees.

The distal femoral referencing guide 4 comprises a superiorly orientated male portion 46 configured for insertion into a corresponding female accommodation 29 of the cutting block guide 5.

The male portion 46 comprises an inferior stop end to limit the travel of the male portion 46 into the female accommodation 29 so as to locate the cutting block guide 5 at an appropriate offset from the inferior condylar apogees for making the distal resection.

In an embodiment, the distal femoral referencing guide 4 is configured for placing the cutting block guide 5 for a distal resection of approximately 9 mm.

Figure 3:
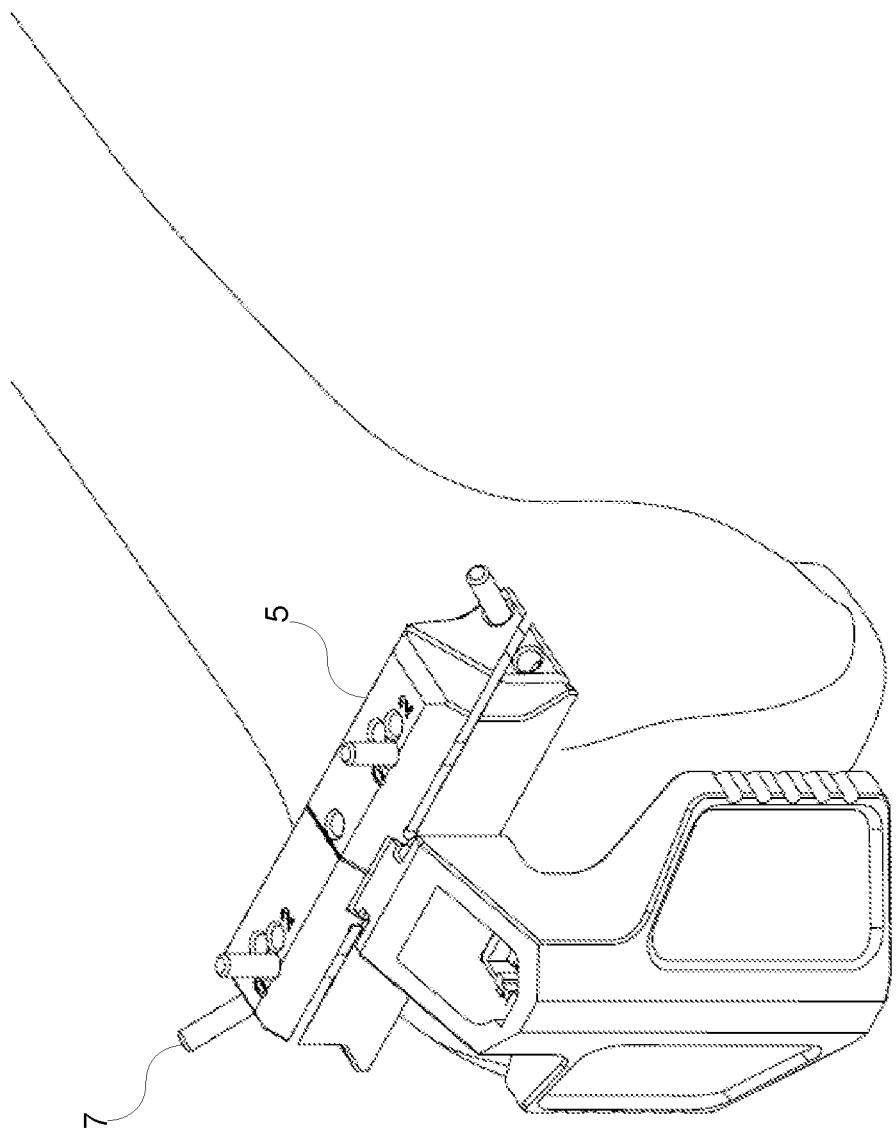
FIG. 3 shows the angled bracket inserted so as to locate the cutting block at an appropriate superior offset (been substantially 9 mm) from the distal condylar apogees for the purposes of making the distal resection.

In FIG. 3, once the laterally projecting condylar contacting flanges 6 of the distal femoral referencing guide 4 make contact with the distal condylar apogees and the cutting block guide 5 therefore suitably placed, fastening pins 7 are inserted into the cutting block guide 5 for securing the cutting block guide 5 to the anterior surface of the femoral epiphysis 2. In the embodiment shown, four fastening pins 7 are provided comprising two fastening pins 7 penetrating at right angles with respect to an anterior face of the cutting block and a further two fastening pins 7 penetrating at substantially 45° through respective lateral/medial faces of the cutting block guide 5.

Figure 4:
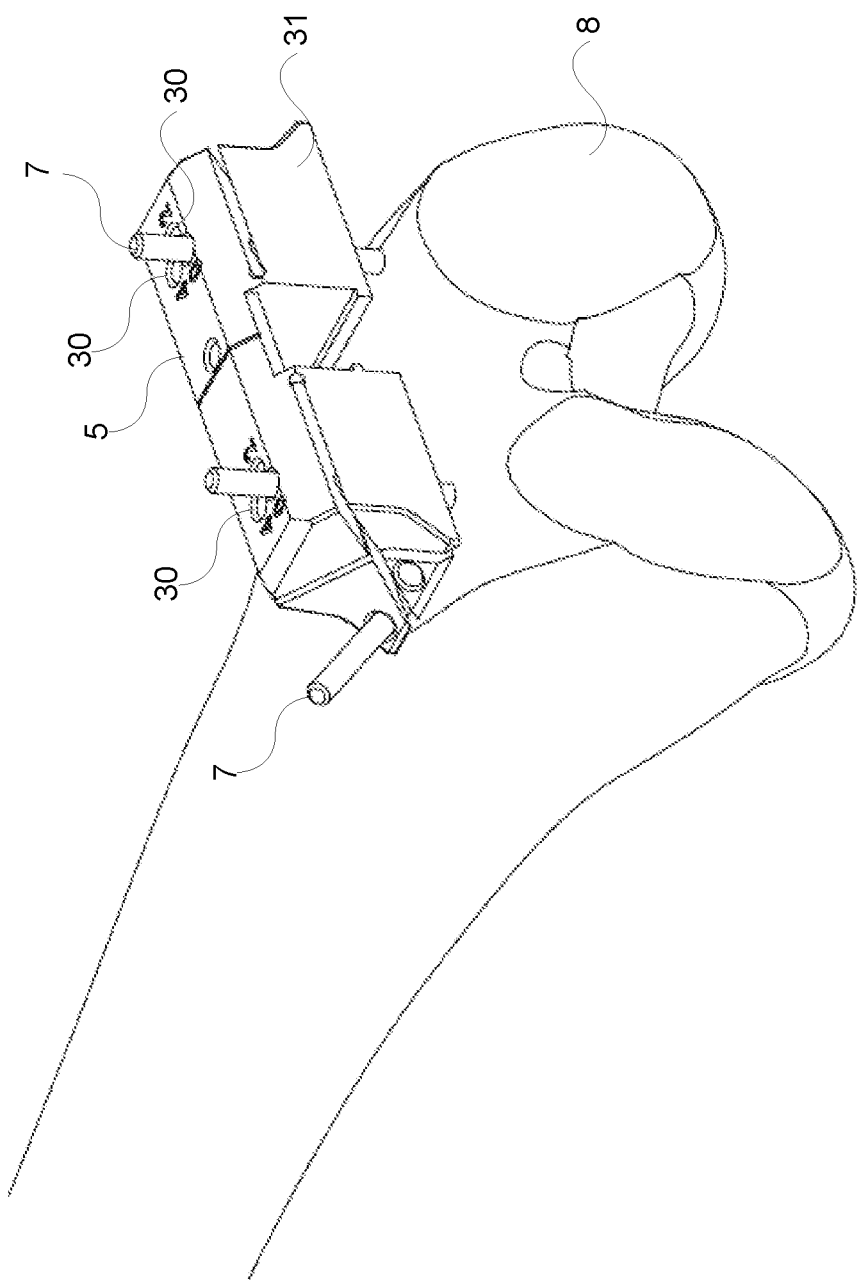
FIG. 4 shows the right angled bracket having been removed with the cutting block left in place and the distal resection having been made.

Turning now to FIG. 4, the distal femoral referencing guide 4 and placement guide 1 are then removed so as to leave the cutting block guide 5 in place fastened to the anterior surface of the femoral epiphysis via the fastening pins 7. In this manner, the cutting block guide 5 presents an inferior face 31 for the purposes of making the distal resection 8.

In embodiments, the cutting block comprises a plurality of fastening pin apertures 30 for placement tolerance. Specifically, as can be seen from FIG. 4, the anterior face of the cutting block guide 5 comprises a plurality of fastening pin apertures 30, located for the purposes of providing lateral/medial placement tolerance and superior/inferior placement tolerance. In an embodiment, the fastening pin apertures 30 may be located substantially 2 mm apart so as to provide for approximately 2 mm of placement tolerance.

Figure 5:
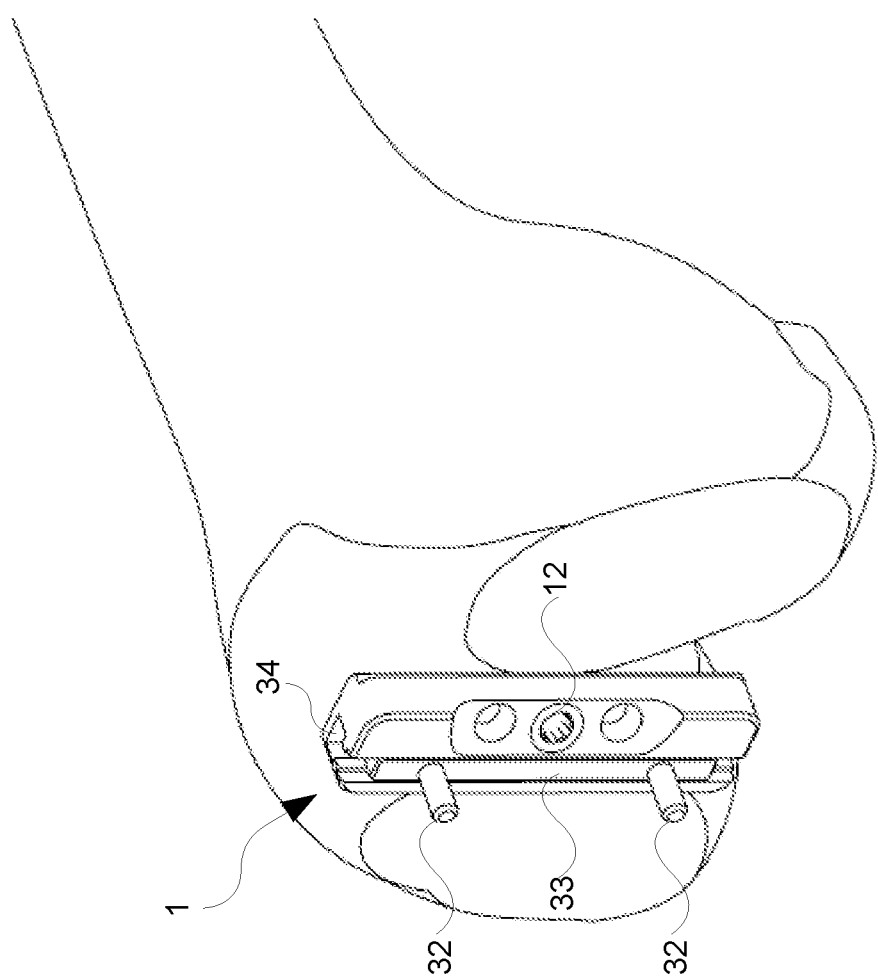
FIG. 5 shows the reinsertion of the placement guide once having made the distal resection.

Once the distal resection 8 has been made, turning now to FIG. 5, the placement guide 1 is reinserted into the aperture 3.

As can be seen from FIG. 5, the placement guide 1 comprises a sliding member 32 configured to slide along an anterior/posterior axis of the femoral epiphysis along a rail 34 for the omni-positioning of the cutting block guide 5 as will be described in further detail below. In this regard, the sliding member 33 comprises two protruding placement guide pins 32 as will also be described in further detail below.

The placement guide 1 comprises a locking pin 12 for locking the sliding member 33 within the rail 34.

Figure 6:
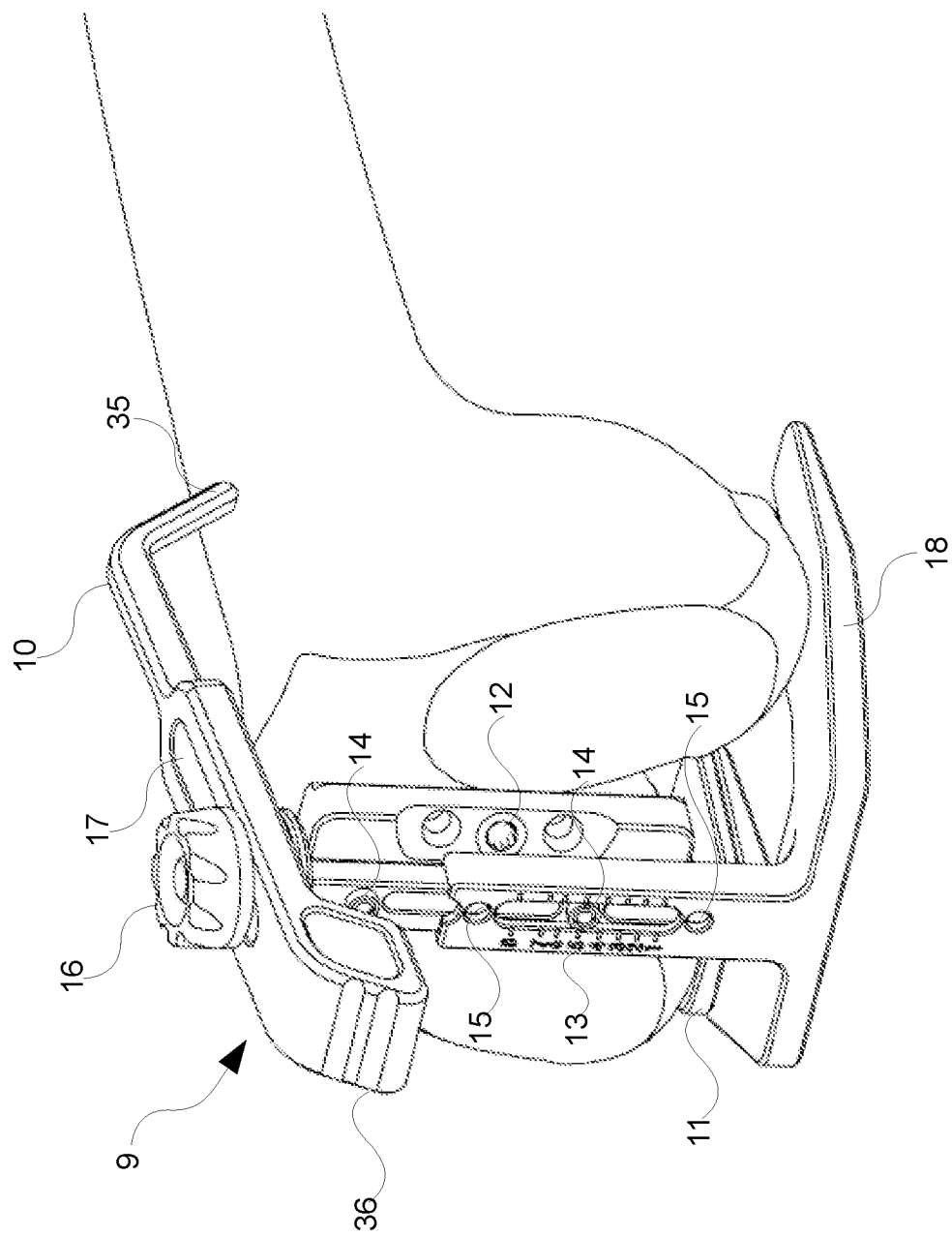
FIG. 6 shows the fastening of a spacer to the placement guide for the purposes of measuring the sizing of the femoral epiphysis and the adjustment of an adjustment mechanism of the placement guide.

Turning now to FIG. 6, a posterior rotational referencing sizing jig 9 is placed over the two protruding placement guide pins 32 of the placement guide 1. The posterior rotational referencing sizing jig 9 is used for the purposes of sizing the femoral epiphysis 2 and for adjusting the anterior/posterior offset of the sliding member 32 within the rail 34. In this regard, the locking pin 12 is left loose so as to allow the sliding member 33 to slide freely within the rail 34.

In the embodiment shown in FIG. 6, the surgeon prefers posterior referencing and has therefore inserted the placement guide pins 32 through posterior reference apertures 14. Conversely, should the surgeon have preferred anterior referencing, the surgeon would have inserted the placement guide pins 32 through the anterior reference apertures 15.

Once having the guide pins 32 to engage the spacer 9, a substantially horseshoe-shaped condylar contacting base 18 of the posterior rotational referencing sizing jig 9 is brought to contact the posterior faces of the femoral condylars and an oppositely located anterior stylus 10 is brought to bear against an interior face of the femur.

When placing the horseshoe-shaped base 18 a spacer 11 may be provided so as to provide approximately 3° of internal rotation. In embodiments, the spacer 11 is removable such that it can be selectively placed on either of the lateral or posterior members of the horseshoe-shaped base 18 for left and right knee prosthesis.

In the embodiment shown, the anterior stylus 10 comprises an elongate aperture 17 and an associated tightening knob 16 for controlling the reach of the anterior stylus 10. Opposite the distal end 35 of the anterior stylus is a grip 36.

As such, the anterior stylus 10 may be extended superiorly for estimating the extent of the interior chamfer resection so as to reduce the potential for stress riser inducing femoral notches.

Figure 7:
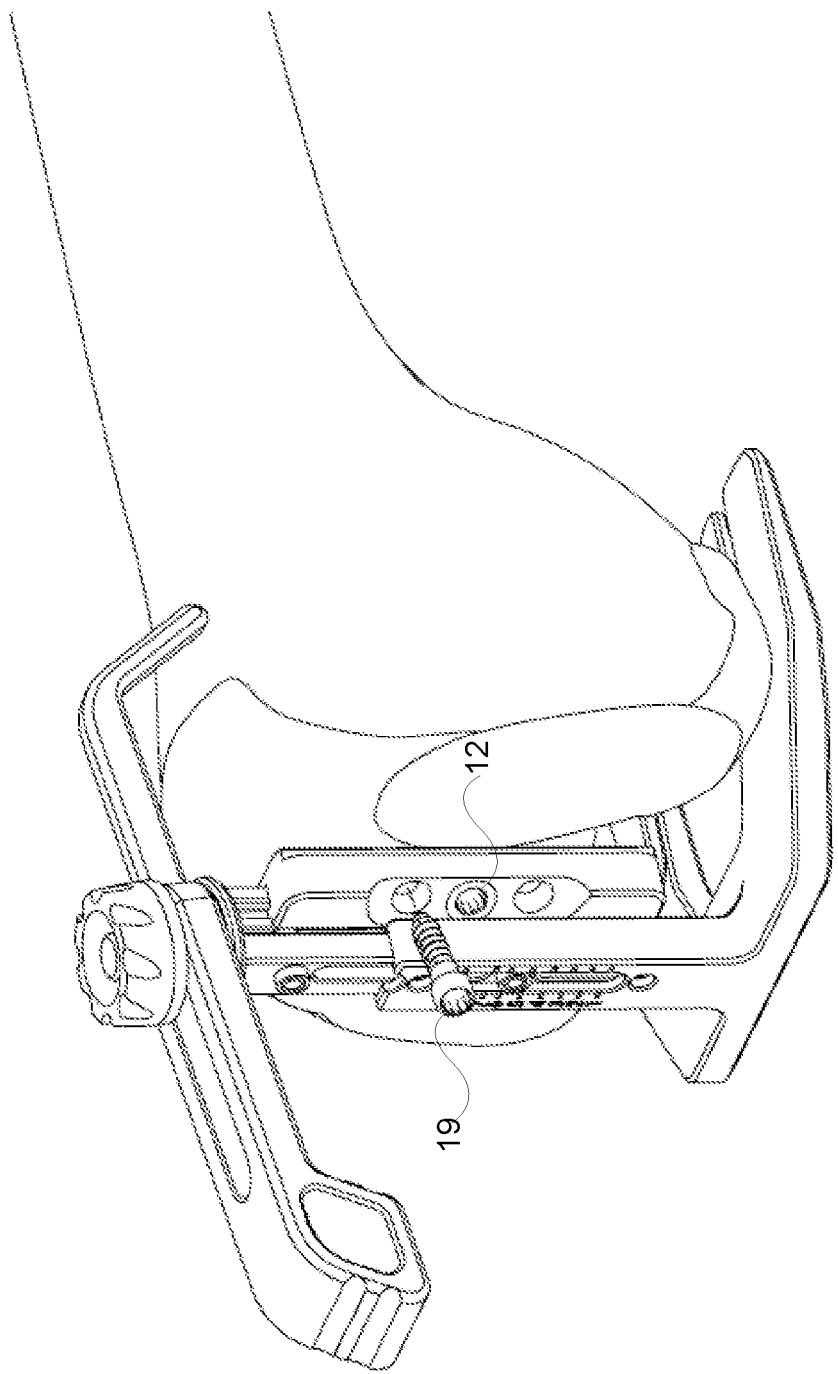
FIG. 7 shows the insertion of a bone fixation screw to fasten the placement guide with respect to the femoral epiphysis and the typing of a locking screw to lock the adjustment mechanism of the placement guide.

Furthermore, turning now to FIG. 7, the anterior stylus 10 may be retracted for performing the sizing. As can be seen, the posterior rotational referencing sizing jig 9 comprises a sizing rule 13 from which the estimated sizing of the femur is read.

As is shown in FIG. 7, once the spacer 9 has been located, the locking screw 12 is tightened so as to lock the sliding member 32 within respect to the rail 34. Furthermore, a further bone fixation screw 19 is inserted through the placement guide 1 so as to prevent the rotation of the placement guide 1 about the rod 27.

Figure 8:
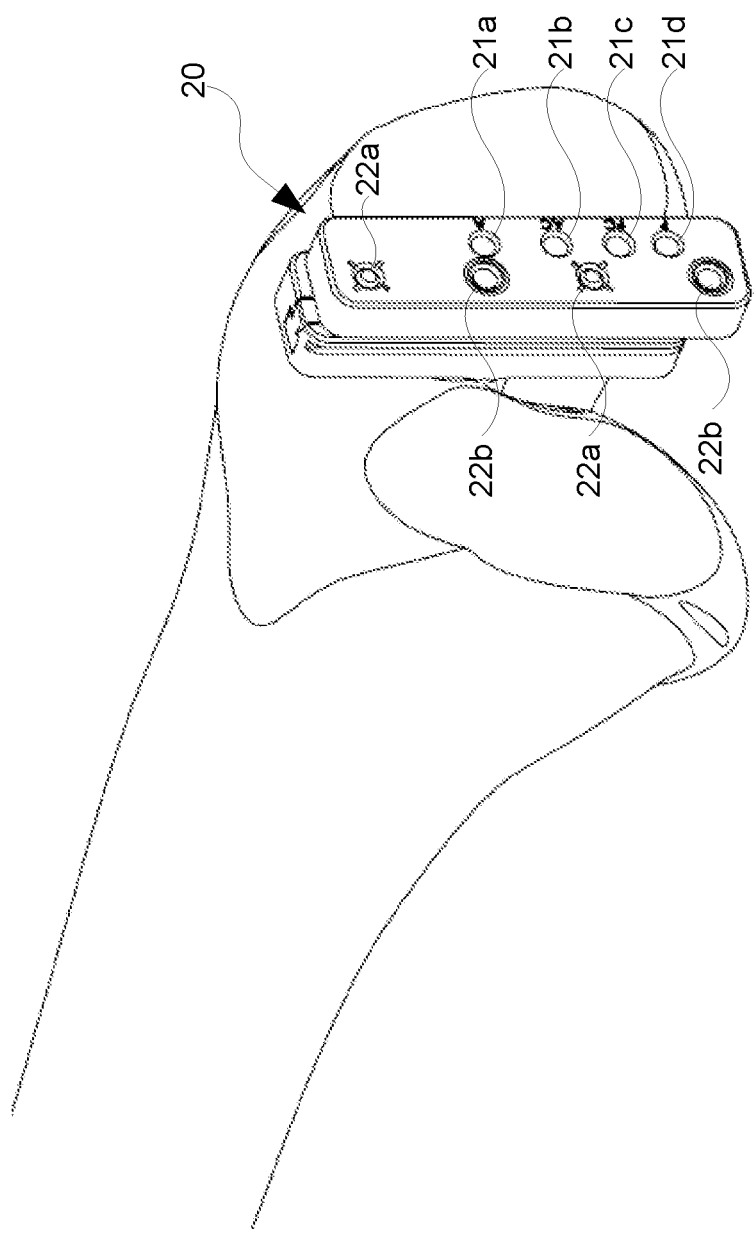
FIG. 8 shows the placement of a punch card over the placement guide.

Turning now to FIG. 8, a punch card 20 is then inserted over the guide pins 32 of the placement guide 1. Specifically, when utilising the posterior reference, the guide pins 32 are inserted through apertures 22a and when utilising the anterior reference the guide pins 32 are conversely inserted through apertures 22b. Apertures 22a and 22b may be marked with appropriate indicia so as to assist the surgeon as to the appropriate utilisation thereof.

As can be seen, the punch card 20 comprises a plurality of punches 21 comprising punch 21a for the purposes of making the anterior resection, punch 21b for the purposes of making the anterior chamfer resection, punch 21c for the purposes of making the posterior chamfer resection and punch 21d for the purposes of making the posterior resection.

Figure 9:
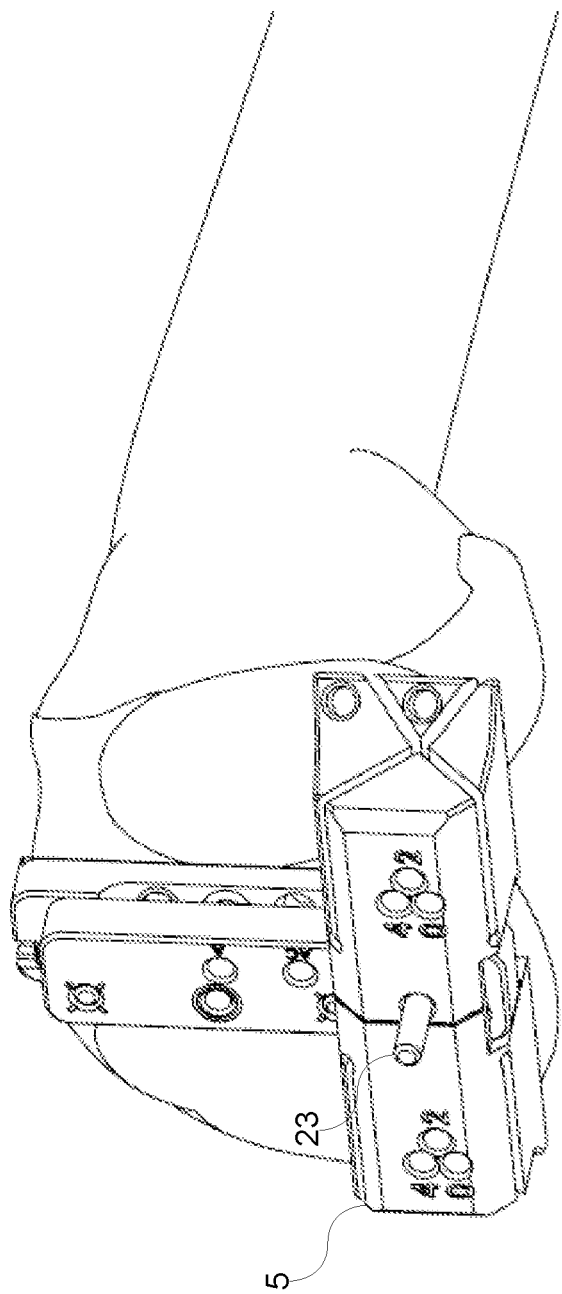
FIGS. 9 and 10 shows the placement of the cutting block with respect to the punch card for the purposes of making the posterior resection.

Specifically, for the purposes of making the posterior resection, and turning now to FIG. 9, the cutting block guide 5 is inserted over the punch card 20 and a fastening pin 23 is inserted through the distal face of the cutting block guide 5 for location within punch 21d.

Figure 10:
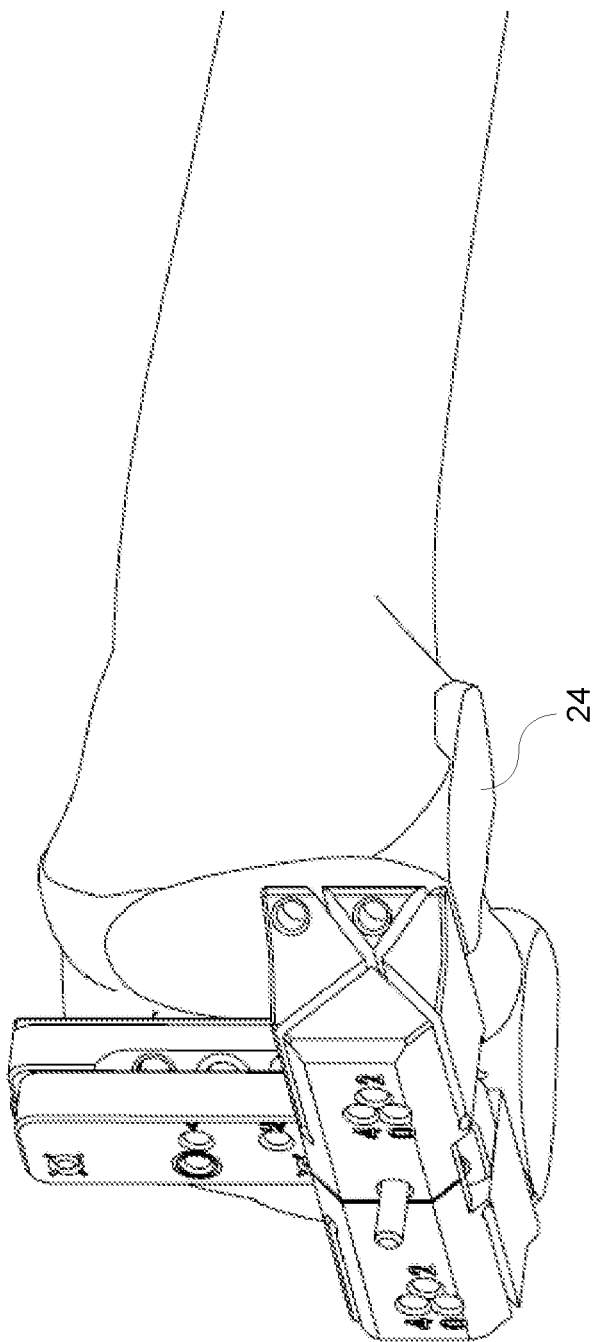

Turning now to FIG. 10, the posterior face of the cutting block guide 5 is utilised for the purposes of making the posterior resection 24.

Figure 11:
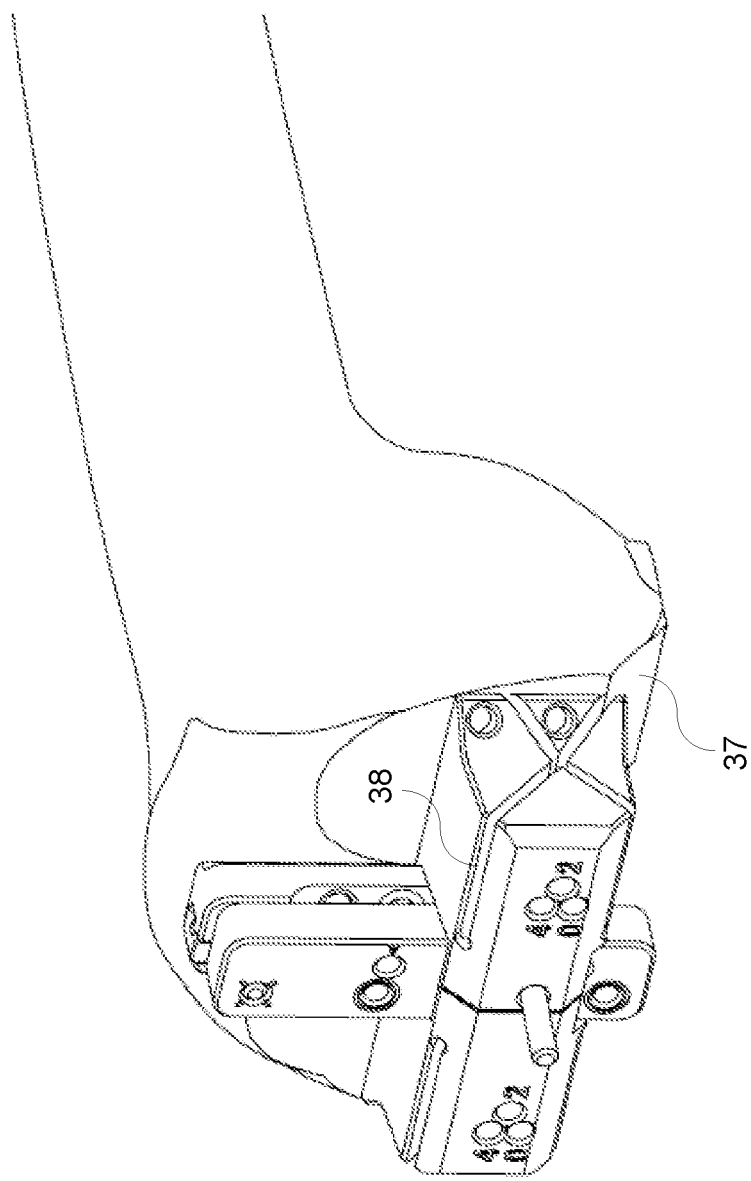
FIG. 11 shows the placement of the cutting block with respect to the punch card for the purposes of making the posterior chamfer resection.

Thereafter, and turning now to FIG. 11, the fastening pin 23 is removed and the cutting block guide 5 is slid along the punch card 20 so as to allow the fastening pin 23 to be inserted into punch 21c for the purposes of making the posterior chamfer resection 37.

As can be seen, the cutting block guide 5 comprises a posterior chamfer resection slot 38 traversing the block 5 at substantially 45° for the purposes of receiving the cutting tool therein for making the posterior chamfer resection 37. As can be seen, the posterior chamfer resection slot 38 does not extend across the entire width of the cutting block guide 5 but is rather bifurcated by being open ended at respective lateral/medial ends of the block 5. Each chamfer resection slot 38 extends far enough towards the midline of the cutting block guide 5 so as to allow the respective condylars to be resected.

Figure 12:
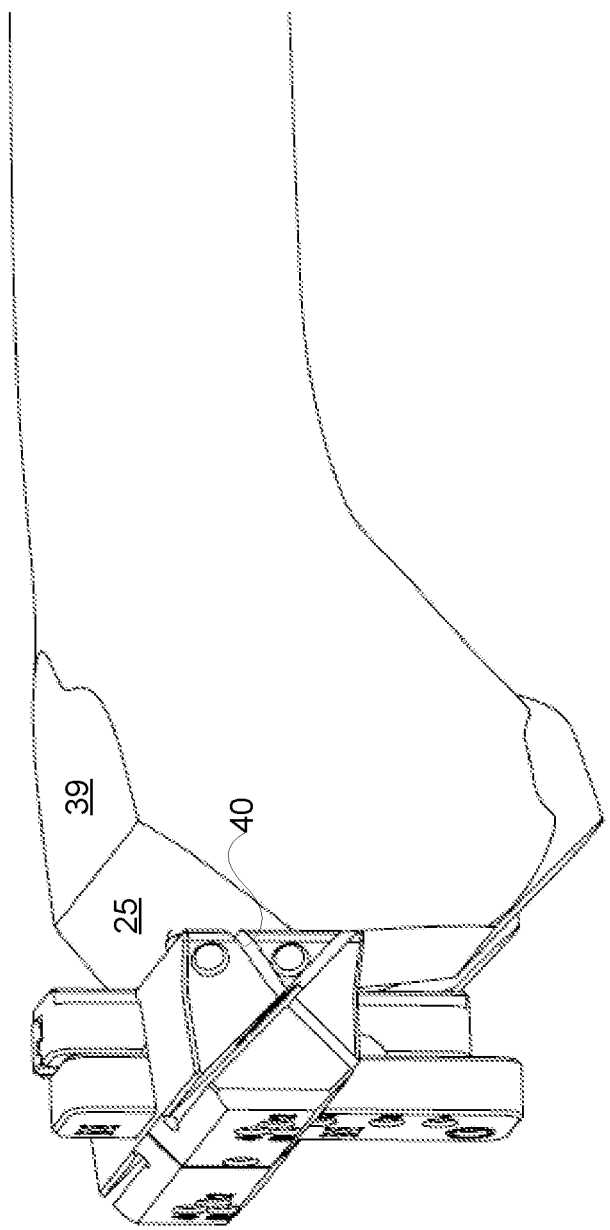
FIG. 12 shows the placement of the cutting block with respect to the punch card for the purposes of making the anterior chamfer and anterior resections.

Turning now to FIG. 12, having made the posterior chamfer resection 37, the fastening pin 23 is again removed so as to allow the guide block 5 to be slid along the punch card 20 so as to allow the fasting pin 23 to be inserted into punch 21a for the purposes of making the anterior resection 39. Specifically, the anterior face of the cutting block guide 5 is used for the purposes of making the anterior resection 39.

Similarly, fasting pin 23 is located into punch 21b for the purposes of making the anterior chamfer resection 25. In this regard, the cutting block guide 5 similarly comprises an interior chamfer resection slot 40 for the purposes of receiving the cutting guide therein for making the anterior chamfer resection 37. As can be seen, the anterior chamfer resection slot 40 is substantially orthogonal to the posterior chamfer resection slot 38.

Figure 13:
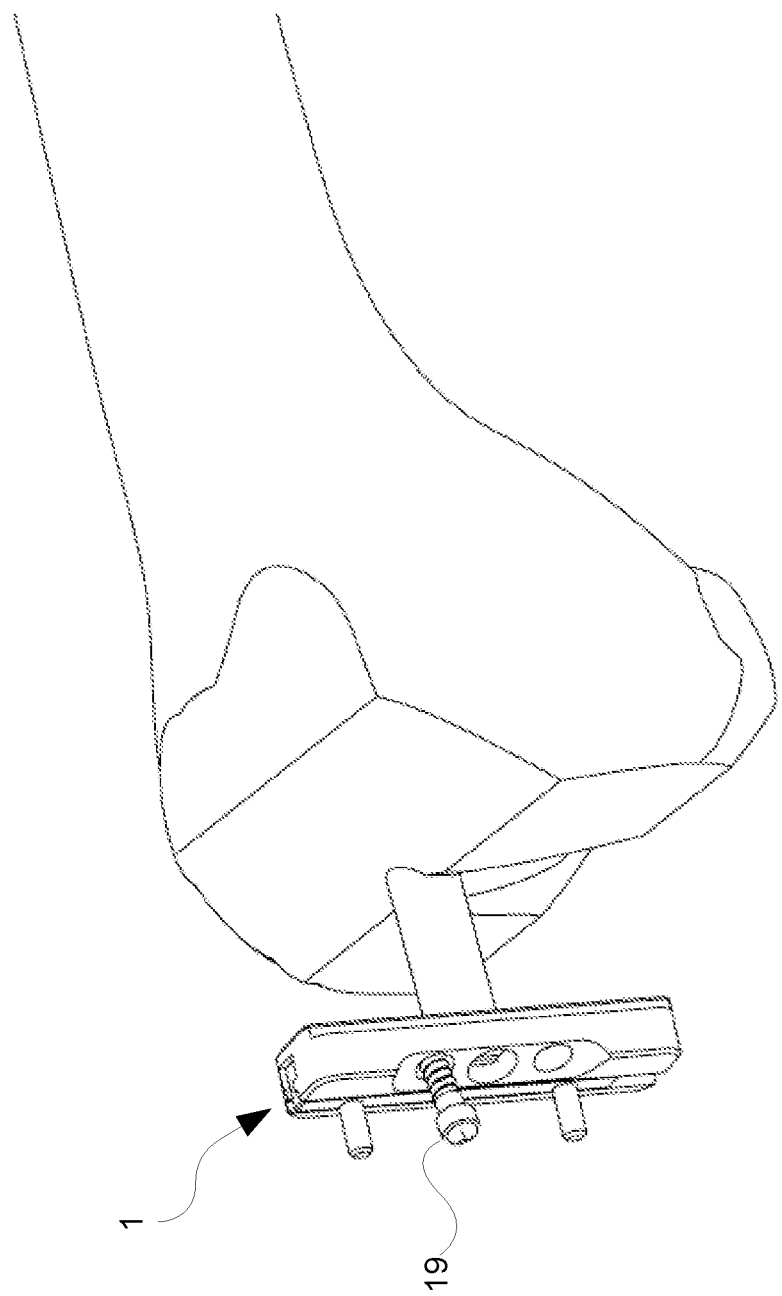
FIG. 13 shows the removal of the placement guide once the resections have been made.

Having made the five resections in the manner described above, turning now to FIG. 13, the fastening screw 19 is loosened and the placement guide 1 is removed.

FIGS. 14-20 show the cutting guide instrumentation in accordance with a further embodiment.

Figure 14:
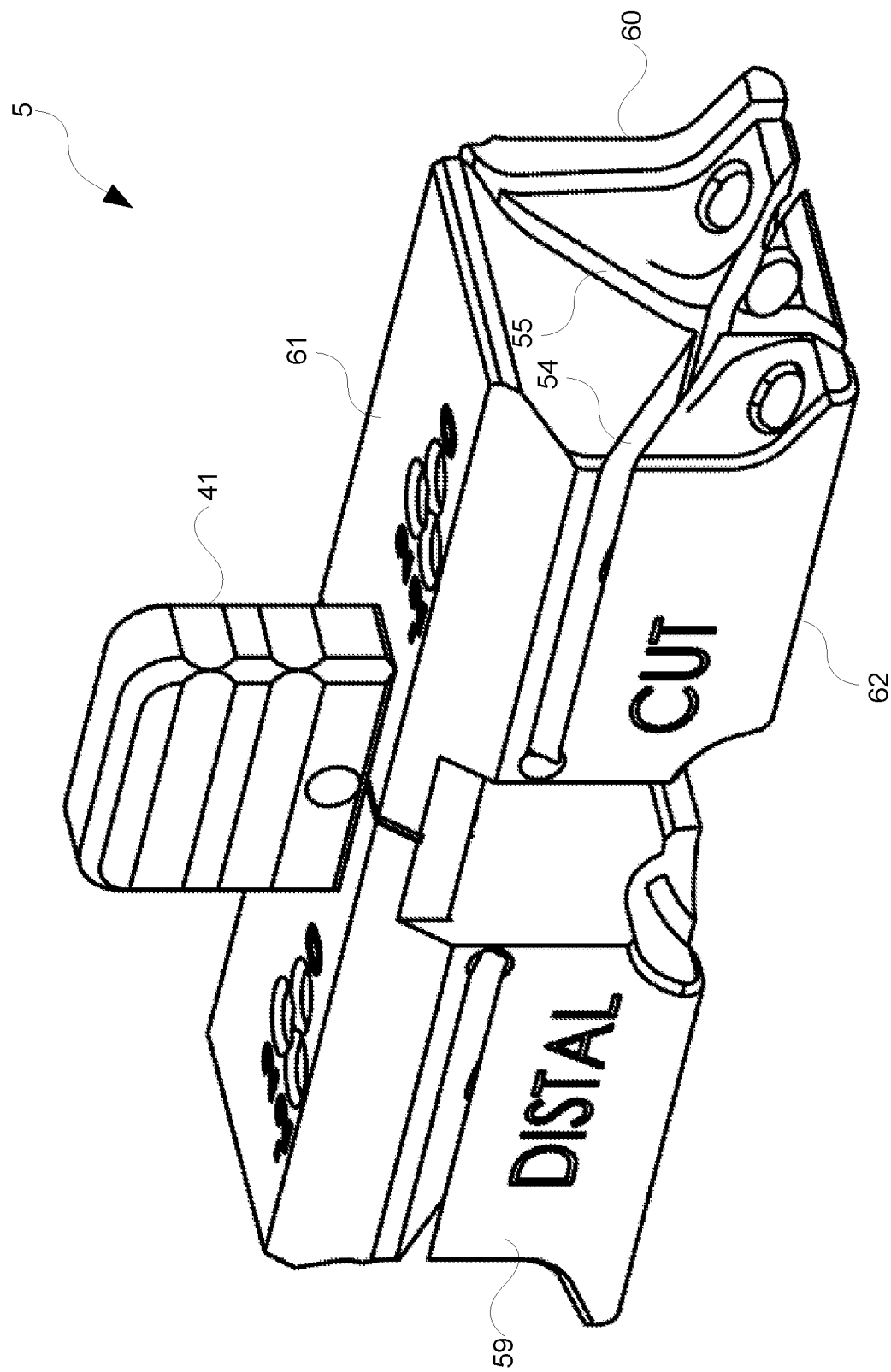

FIG. 14 shows the cutting block guide 5 in accordance with this further embodiment. As is immediately apparent, the cutting block guide 5 includes a locking tab 41.

The cutting block guide 5, and as alluded to above, is able to guide six resections including distal femoral, proximal tibial, anterior femoral, anterior femoral chamfer, posterior femoral chamfer and posterior femoral resections.

Figure 15:
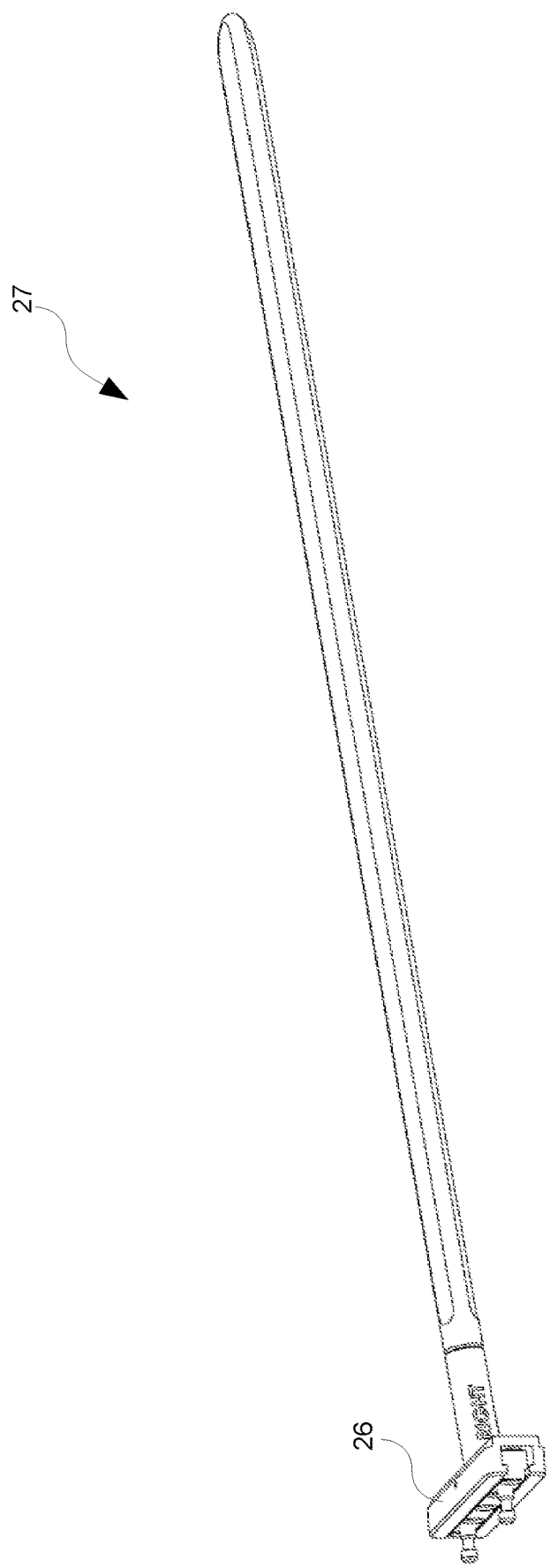

FIG. 15 shows the rod 27 and the orthogonal distal guide portion 28. The orthogonal distal guide portion 28 is orientated 6° from the orthogonal axis of the rod 27 which is used to determine the valgus orientation.

FIG. 16 shows the distal femoral referencing guide 4 which is utilised to determine the amount of the distal femur resected.

Figure 17:
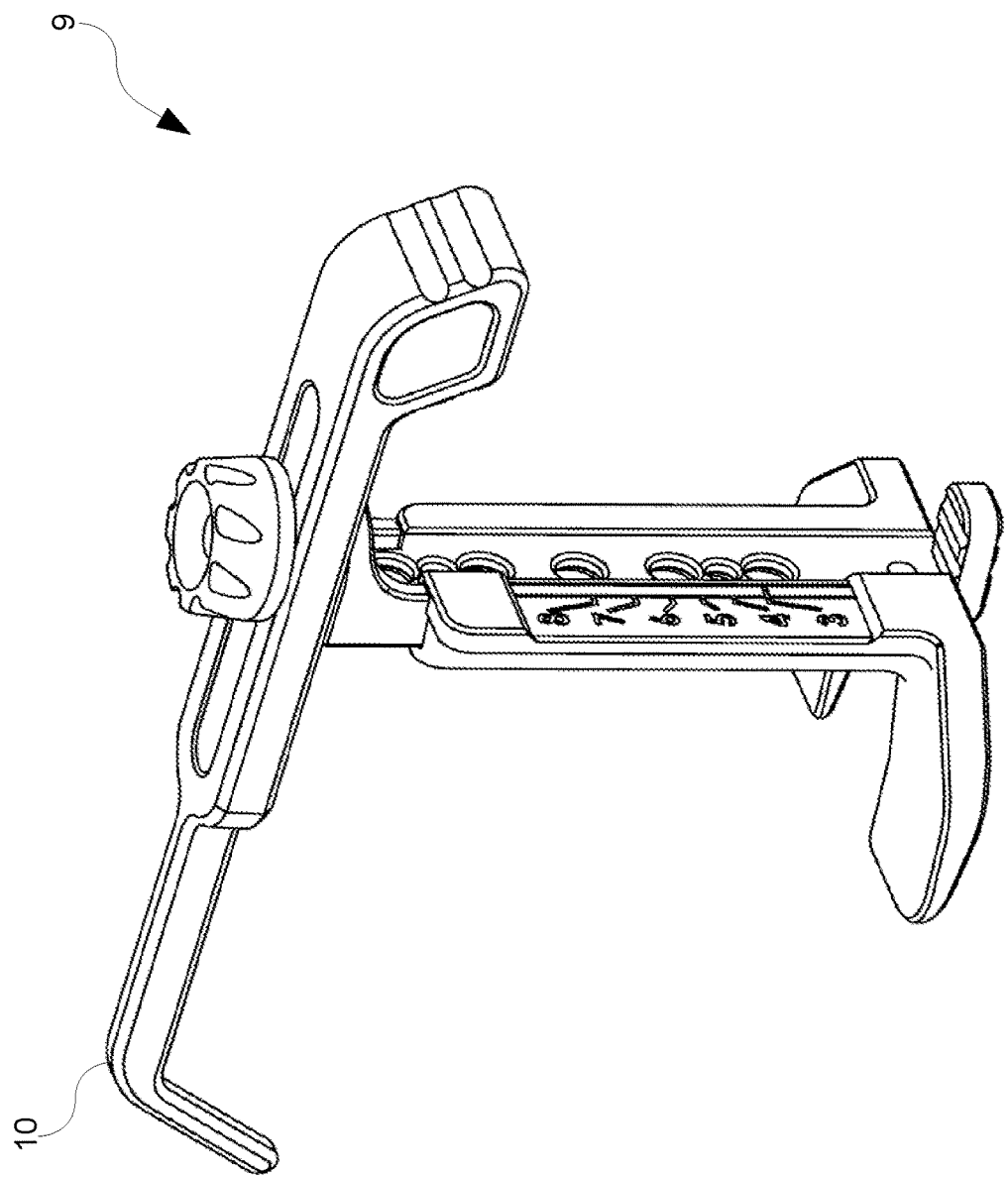
Figure 18:
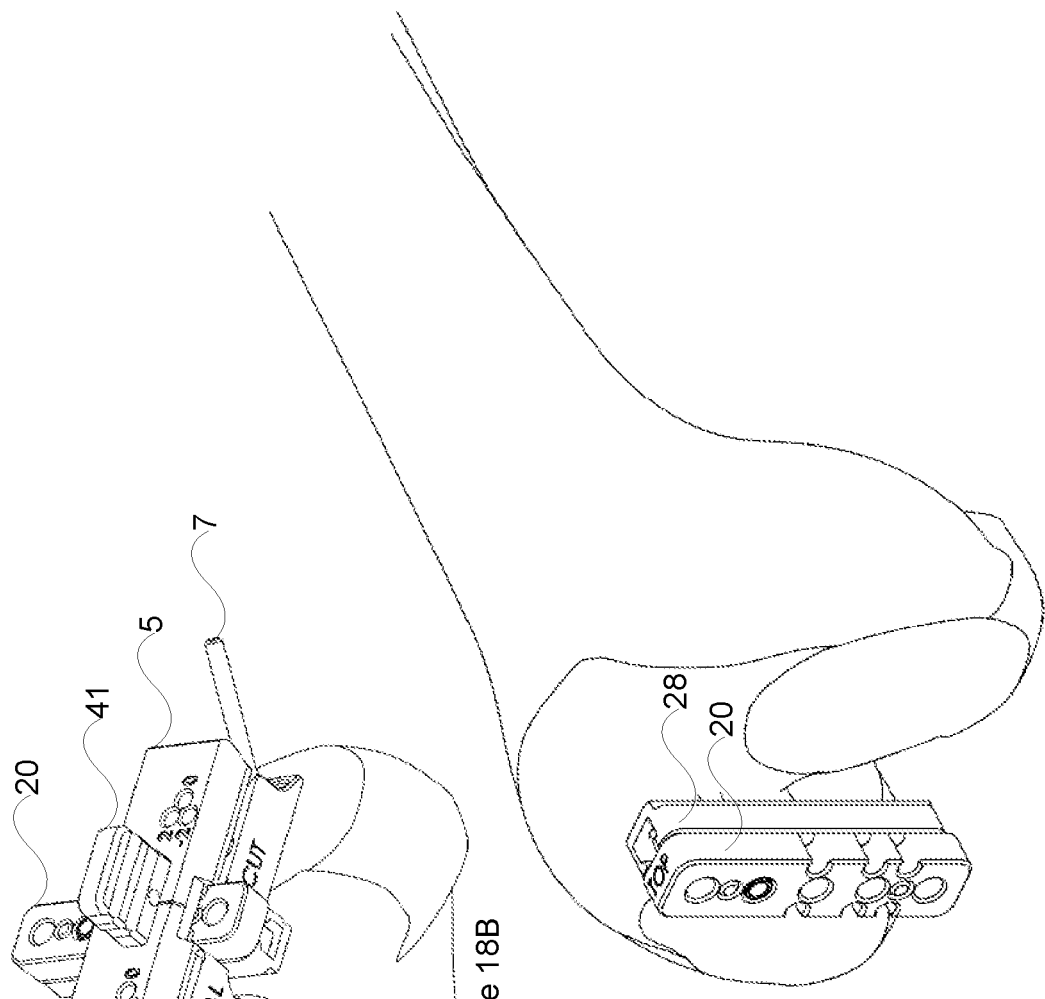

FIG. 17 shows the posterior rotational referencing sizing jig 9 with the anterior stylus 10 wherein the jig 9 and the stylus 10 guide the degree of external rotation of the femoral resections made with the cutting guide 5 and the size of the femur.

FIG. 18A illustrates the punch card 20 engaging the orthogonal distal guide portion 28 of the rod 27 and FIG. 18B shows the cutting block guide 5 being secured to the punch card 20 utilising the locking tab 41 and being held in place on the resected femur utilising fastening pins 7.

Figure 19:
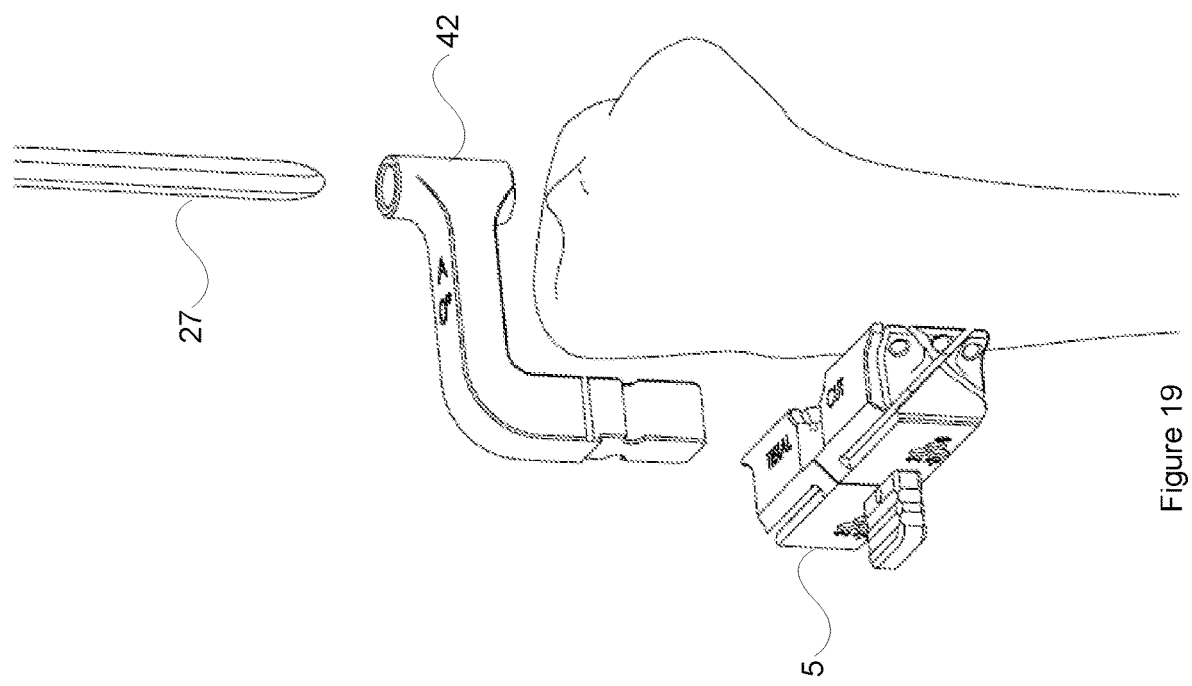

FIG. 19 shows an inter-tibial coupler 42 utilised to couple the cutting block guide 5 to the rod 27 for making the tibial proximal resection.

Figure 20:
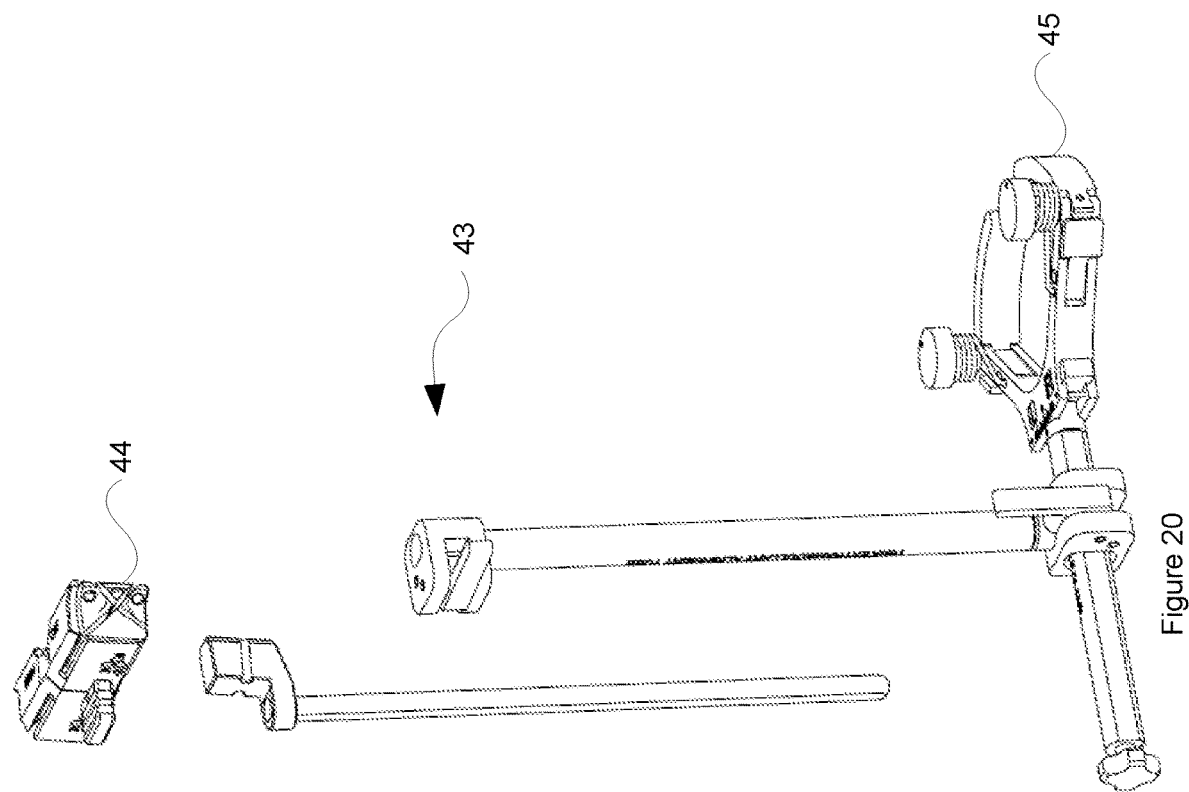

FIG. 20 shows an extramedullary tibial coupler 43 used to attach the cutting block guide 5 to a standard ankle clamp 45 without the use of an intramedullary rod 27.

Figure 21:
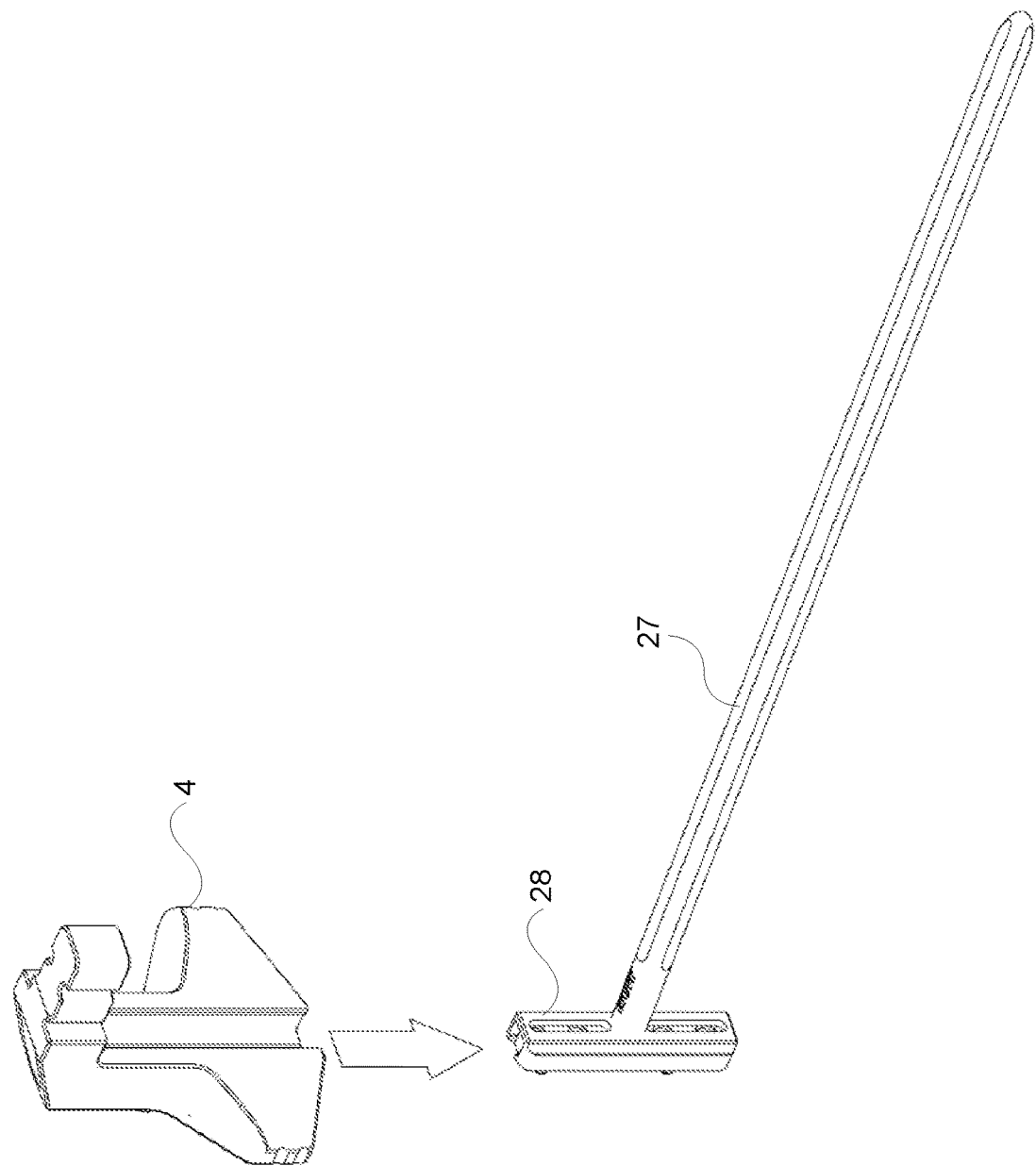
FIG. 21-37 show an exemplary method of the utilisation of the cutting guide instrumentations FIGS. 14-20.

Now, describing the methodology of the utilisation of the guide 1 in accordance with the further embodiment provided in FIG. 14-20, reference is now made to FIG. 21 wherein the distal femoral referencing guide 4 is attached to the 6° valgus offset orthogonal distal guide portion 28 of the rod 27. As can be seen, the referencing guide 4 slides onto the guide portion 28.

Figure 22:
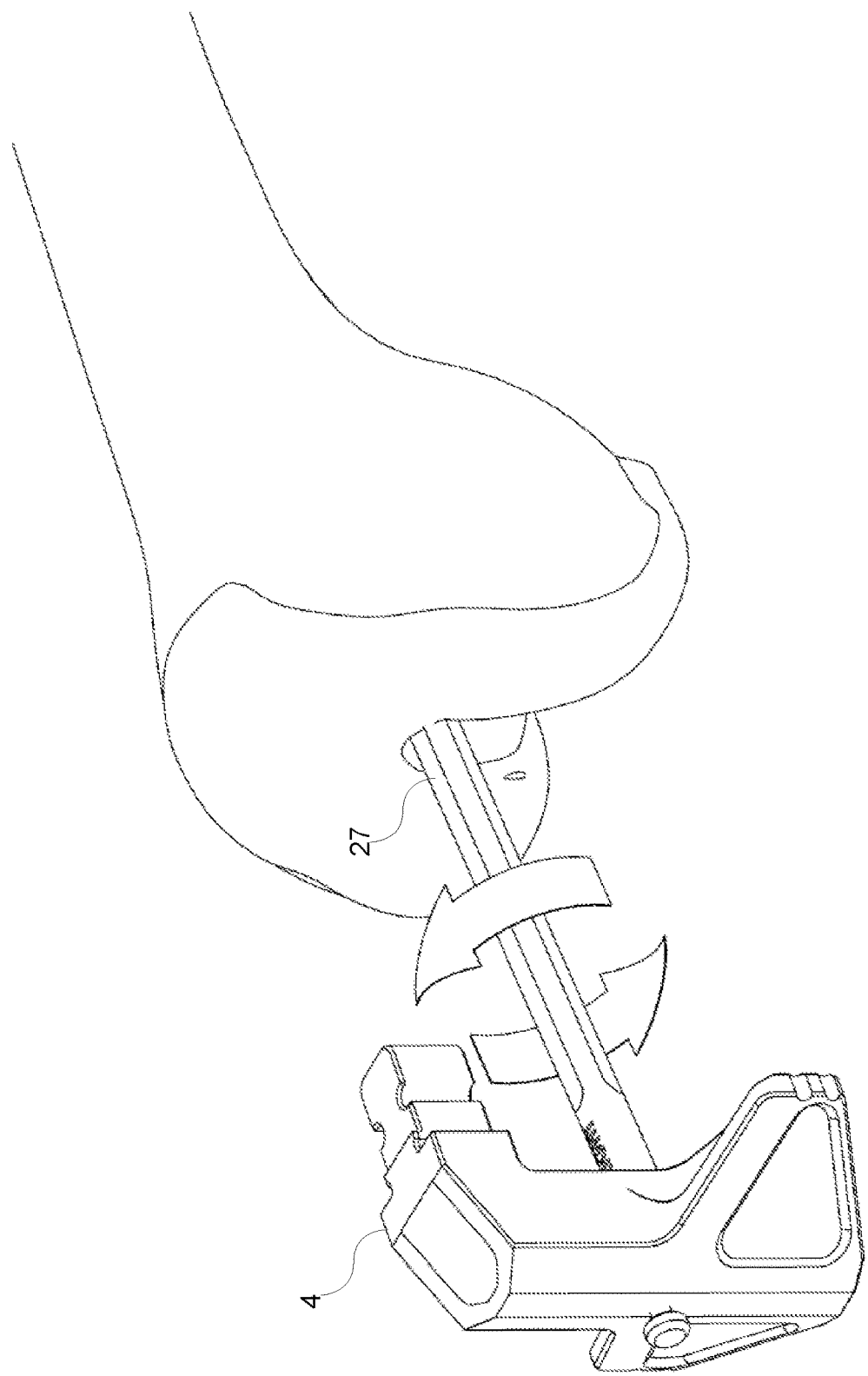

FIG. 22 shows the intermedullary canal having been drilled and the rod 27, having the femoral referencing guide 4 attached thereto, inserted into the canal.

As alluded to above, the orthogonal distal guide portion 28 has a valgus offset of 6° from the orthogonal axis of the rod 27 and can be flipped within the canal for left or right knees.

Figure 23:
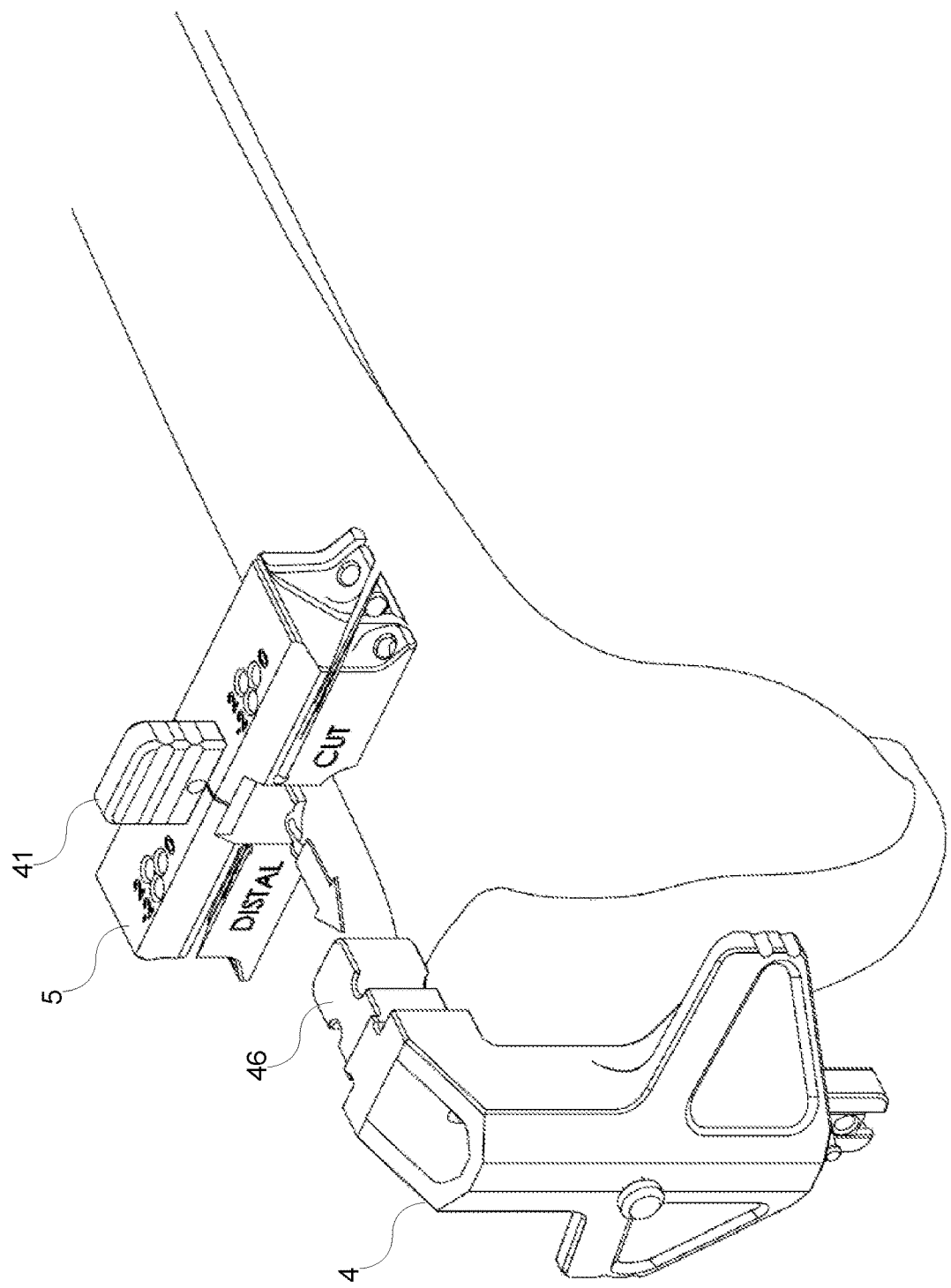

Turning to FIG. 23, the cutting block guide 5 is attached to the referencing guide 4 for the purposes of making the distal cut.

Figure 24:
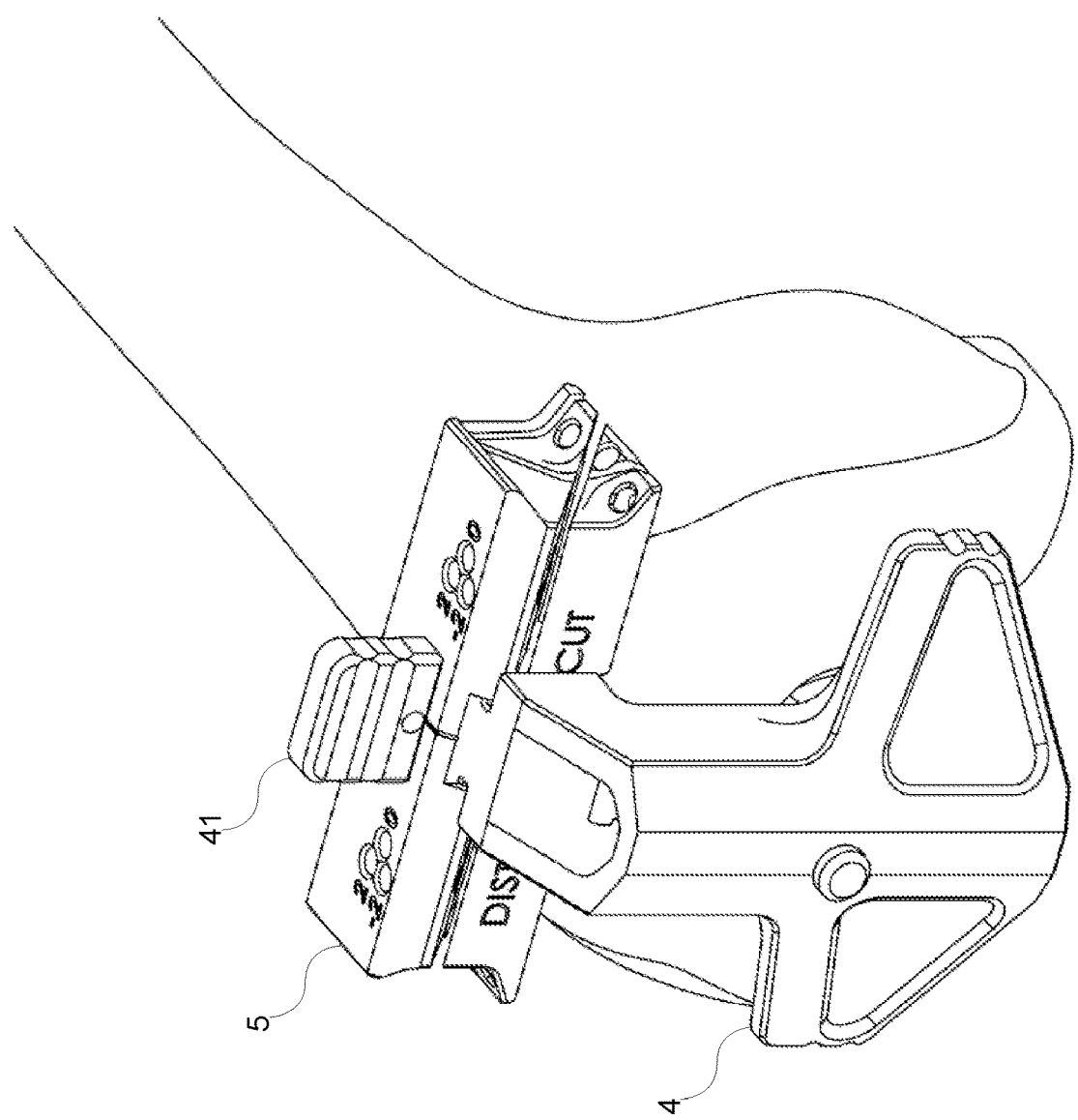

For attaching the cutting block guide 5 to the referencing guide 4, the tab 41 is pulled so as to allow the cutting block to slide onto the male portion 46 of the distal femoral referencing guide 4 wherein, once located, the tab 41 is released to capture the male portion 46 as a substantially shown in FIG. 24.

In FIG. 24, the distal femoral referencing guide 4 is pushed against the distal condyles so as to suitably locate the cutting block guide 5. The distal femoral referencing guide 4 and the cutting block guide 5 are configured so as to provide 9 mm of resection.

Figure 25:
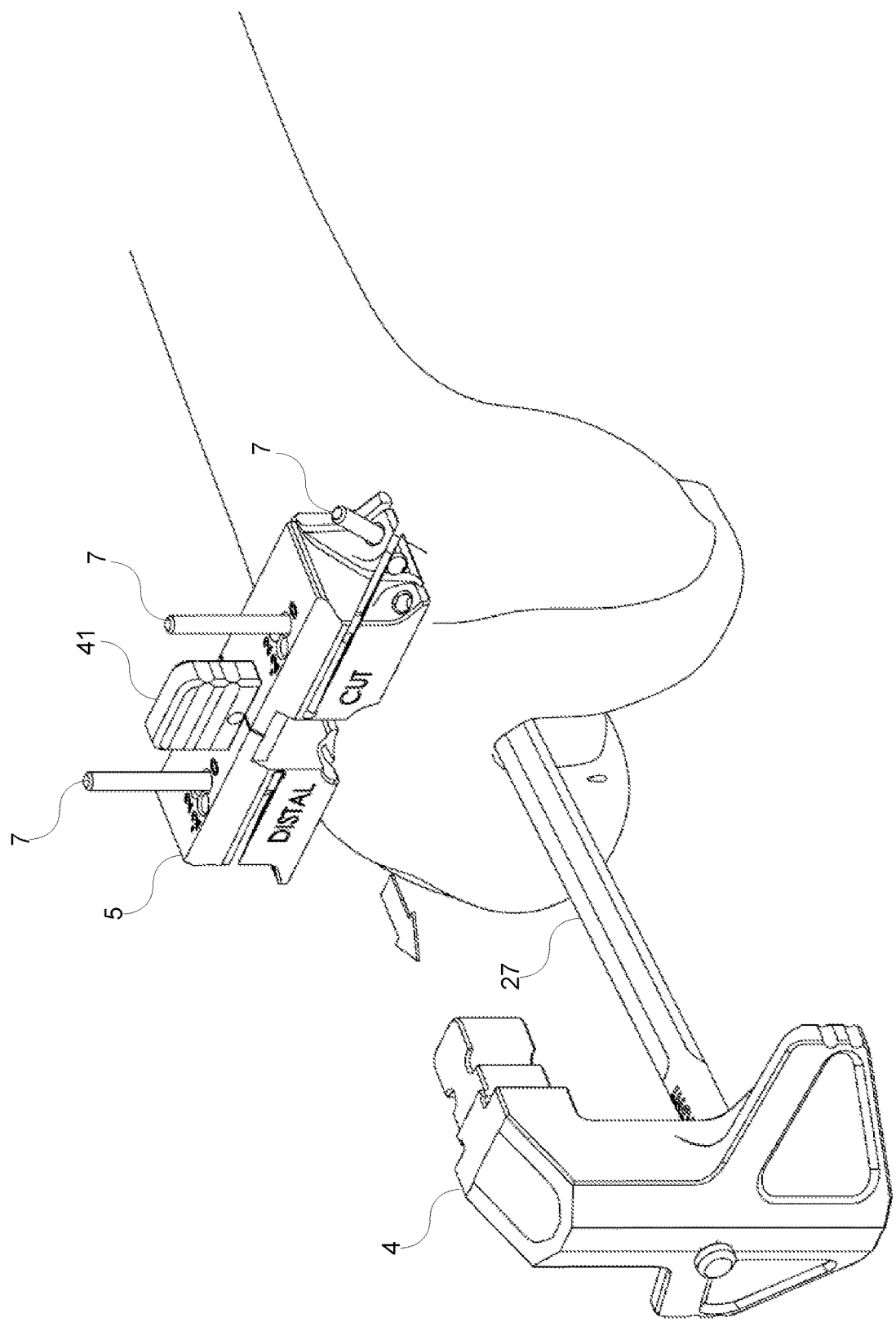

Turning now to FIG. 25, with the cutting block guide 5 having been suitably located with reference to the distal femoral referencing guide 4, the cutting block guide 5 is secured in place with fastening pins 7 and the locking tab 4 pulled so as to allow the release of the distal femoral referencing guide 4 and rod 27.

Figure 26:
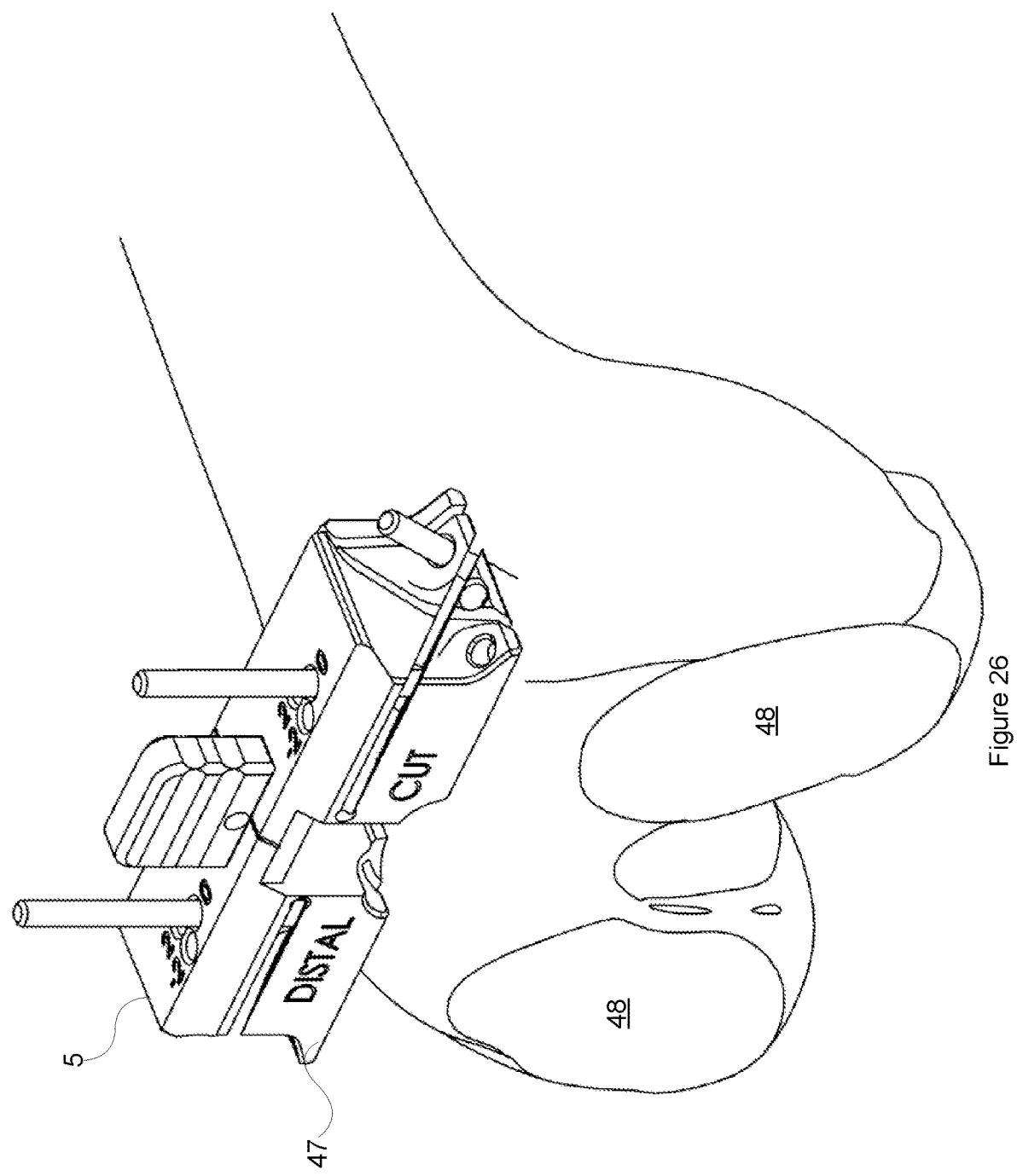

FIG. 26 shows the distal resection 48 having been made with reference to the distal face 47 of the cutting block guide 5.

Figure 27:
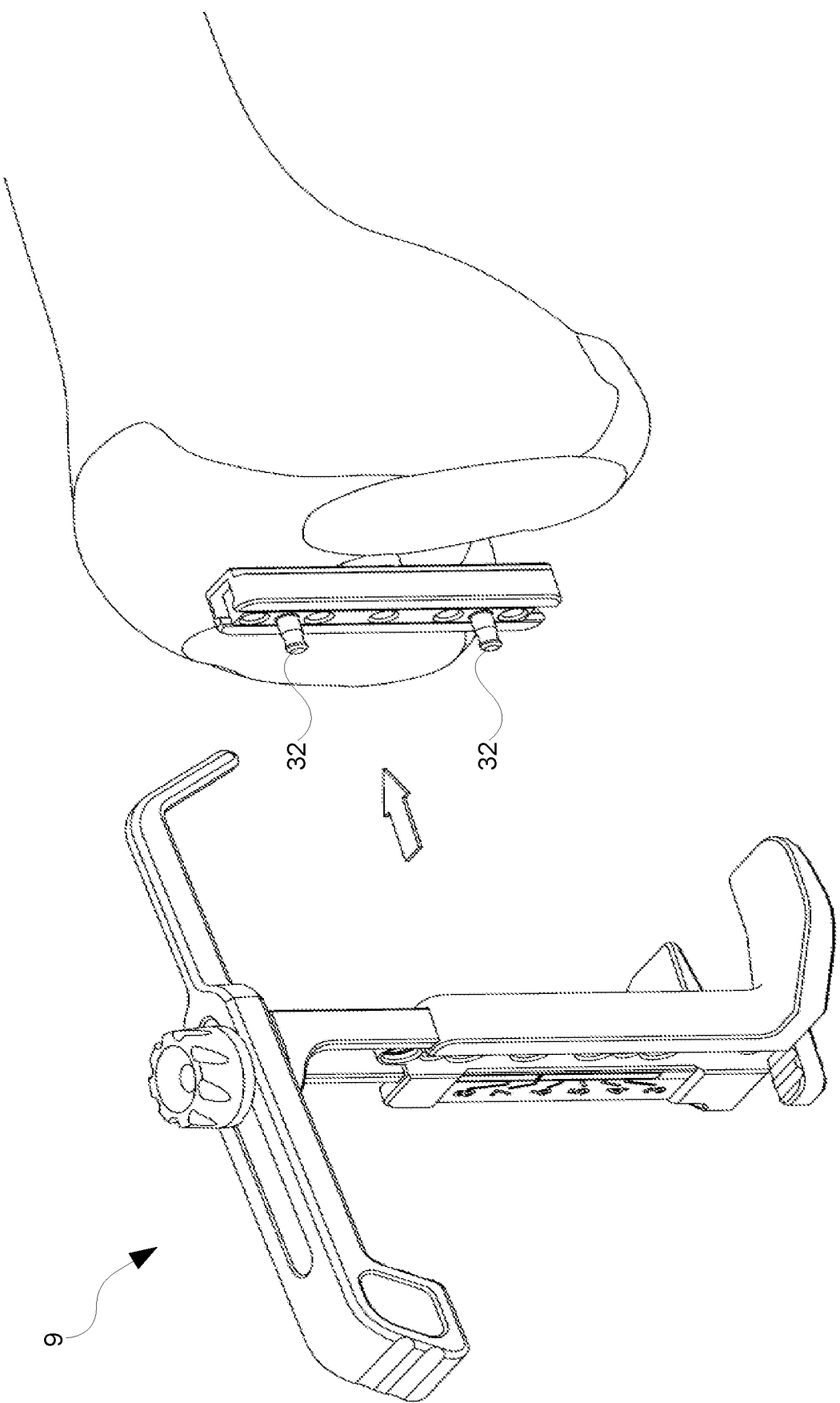

FIG. 27 shows the re-insertion of the intermedullary rod 27 into the femoral canal and the placement of the sizing jig 9 on the slidable placement pins 32 of the orthogonal distal guide portion 28. The sizing jig 9 clicks into position on the pins 32.

Figure 28:
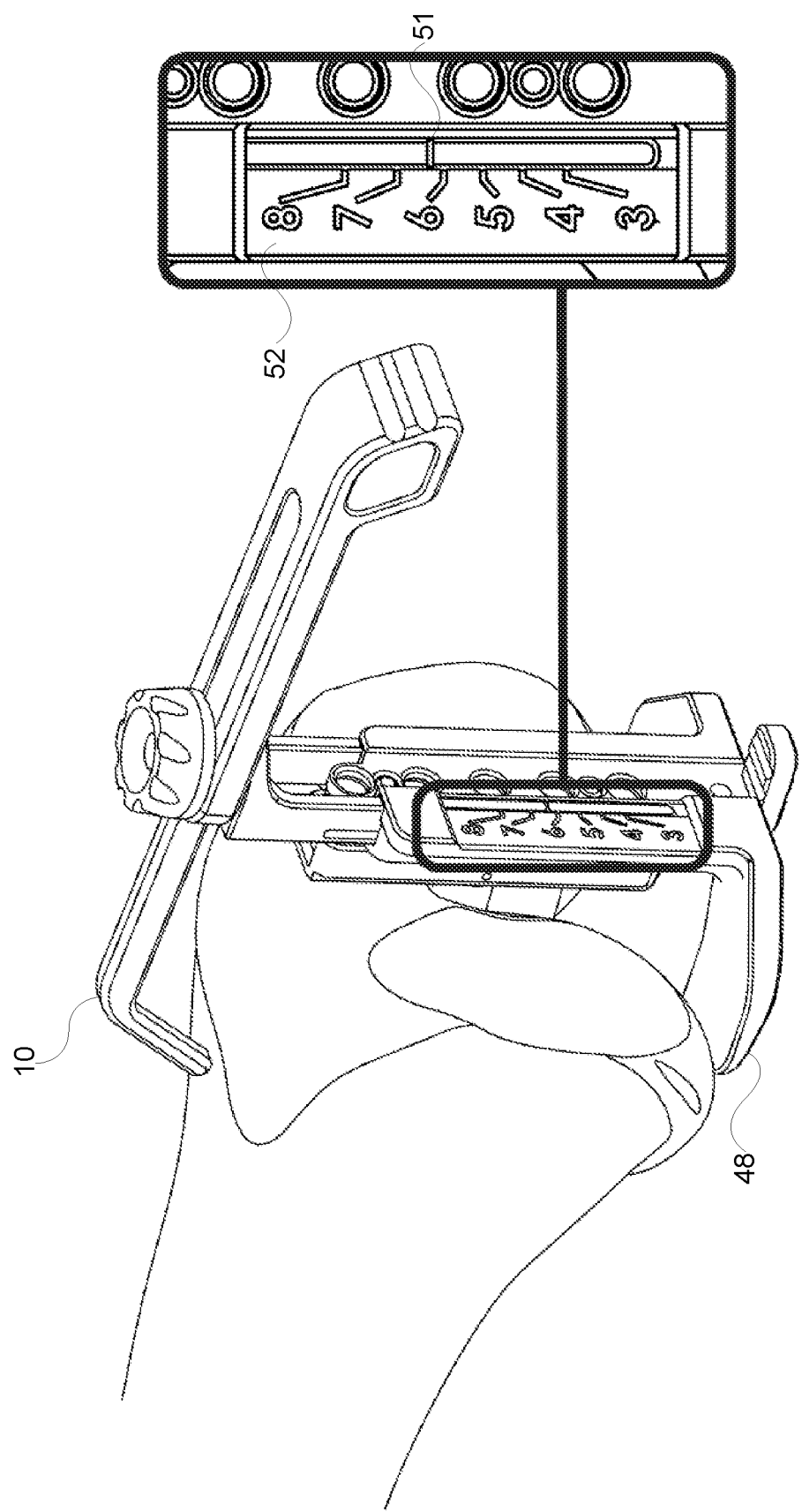
Figure 29:
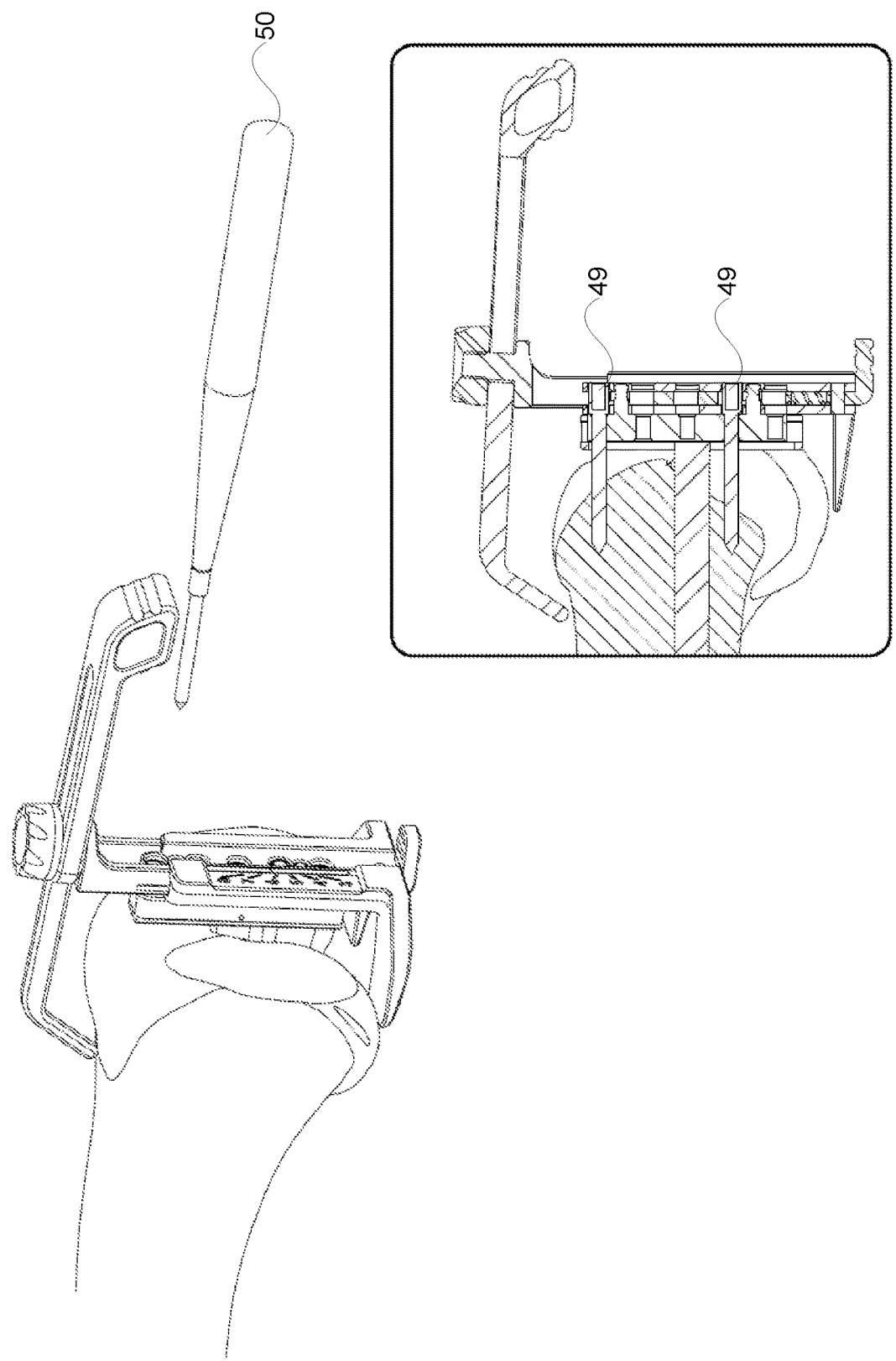

FIG. 28 shows the stylus 10 and the foot 48 of the jig 9 being used to reference the anterior lip and posterior condyles respectively so as to determine the sizing and the rotation of the femur. The sizing of the femur may be read utilising the position of the indicator 51 on the sizing rule 52.

Turning to FIG. 28, with the correct size and rotation having been determined, locking pins are 49 driven through the sizing jig 9 with driver 50 to fix the positions of the slidable placement pins 32.

Figure 30:
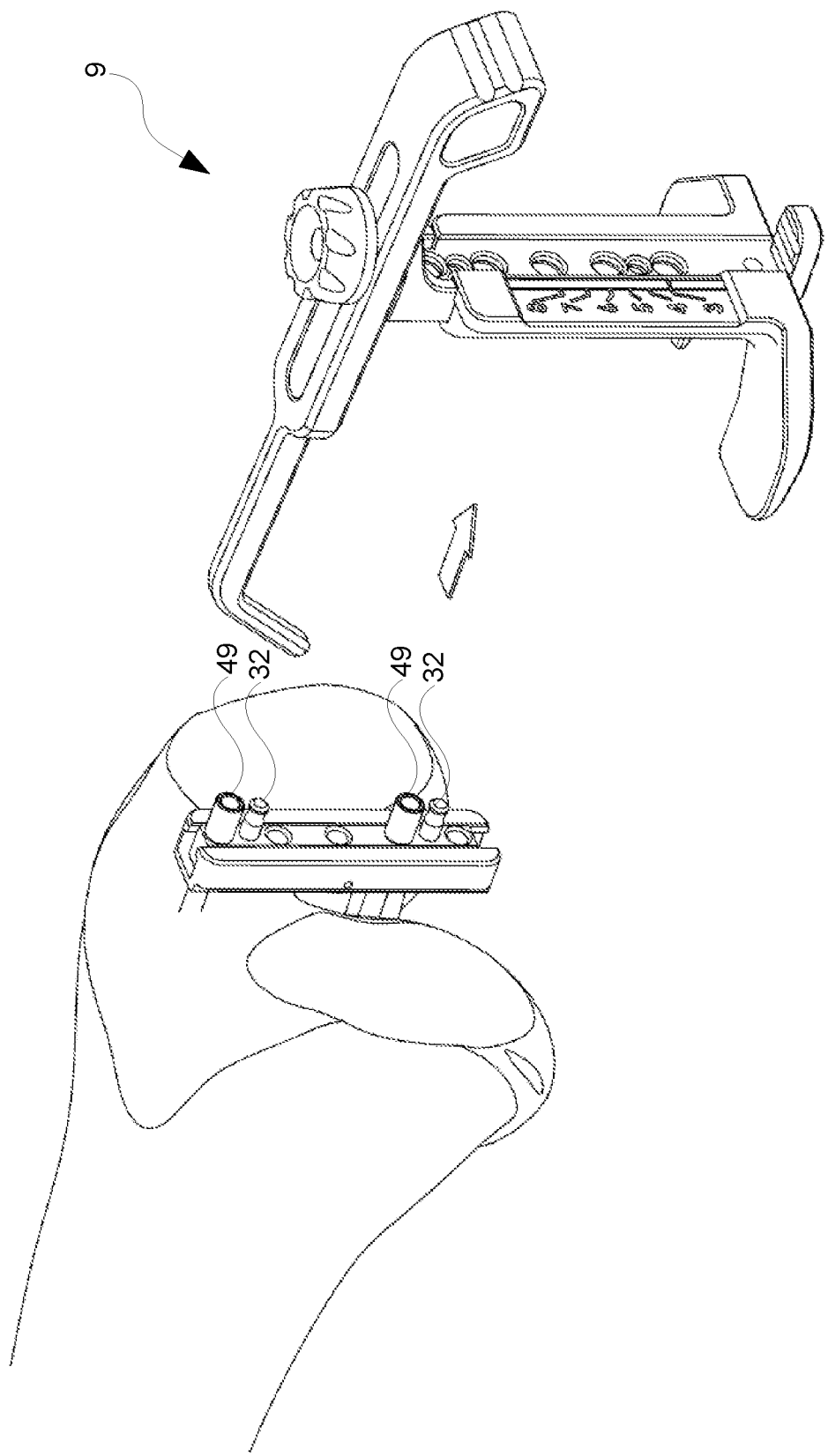
Figure 31:
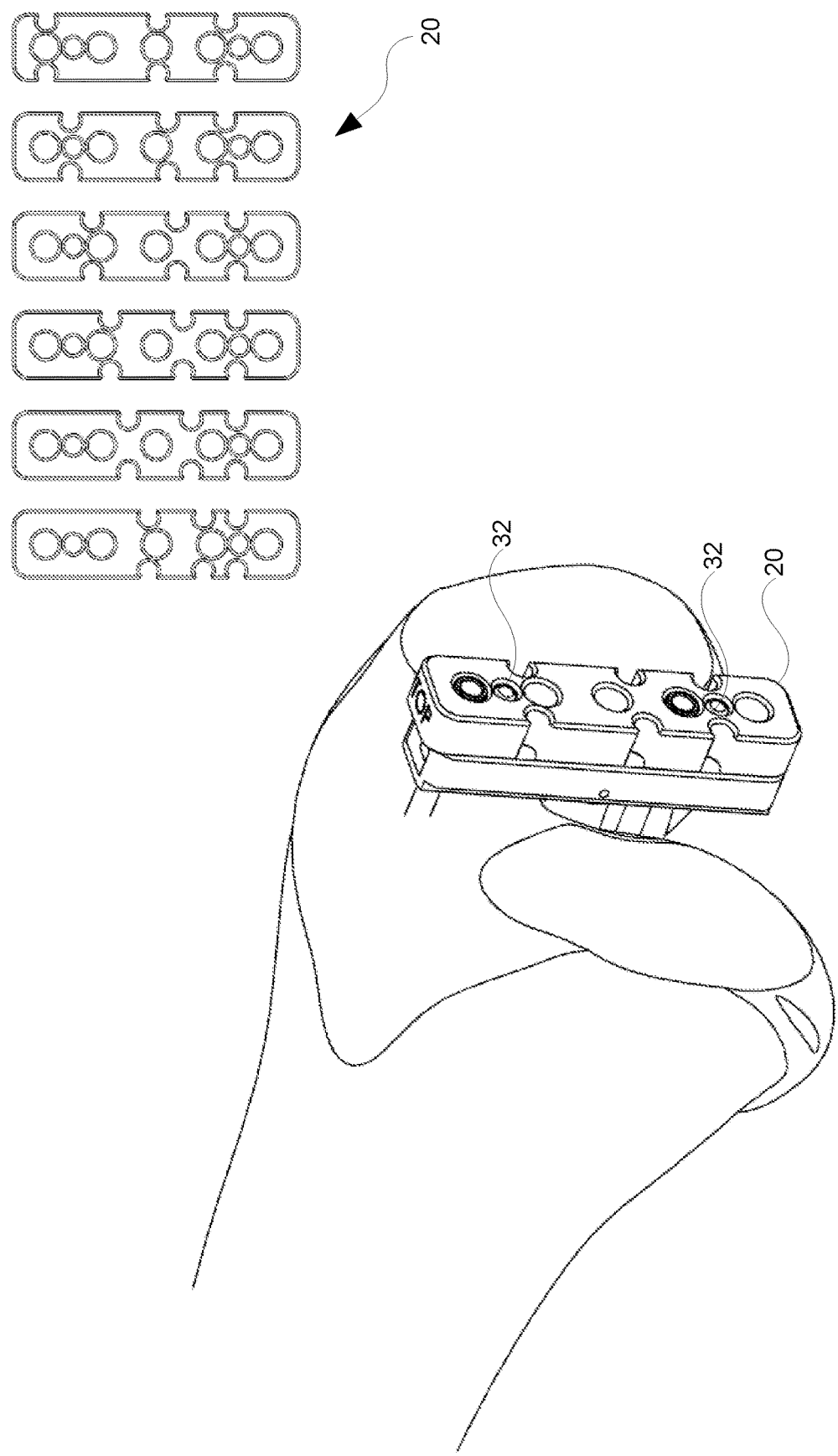

Turning now to FIG. 30, there is shown the sizing jig 9 being removed from the placement pins 32 wherein the placement pins 32 are fixed in place utilising locking pins 49.

Once the sizing jig 9 has been removed, a punch card 9 corresponding to the sizing determined from the sizing rule 52 is selected. Specifically, punch cards 20 may be provided ranging in size from 3-8 wherein, once the appropriate size has been selected, the punch card 20 is placed over the placement pins 32.

Figure 32:
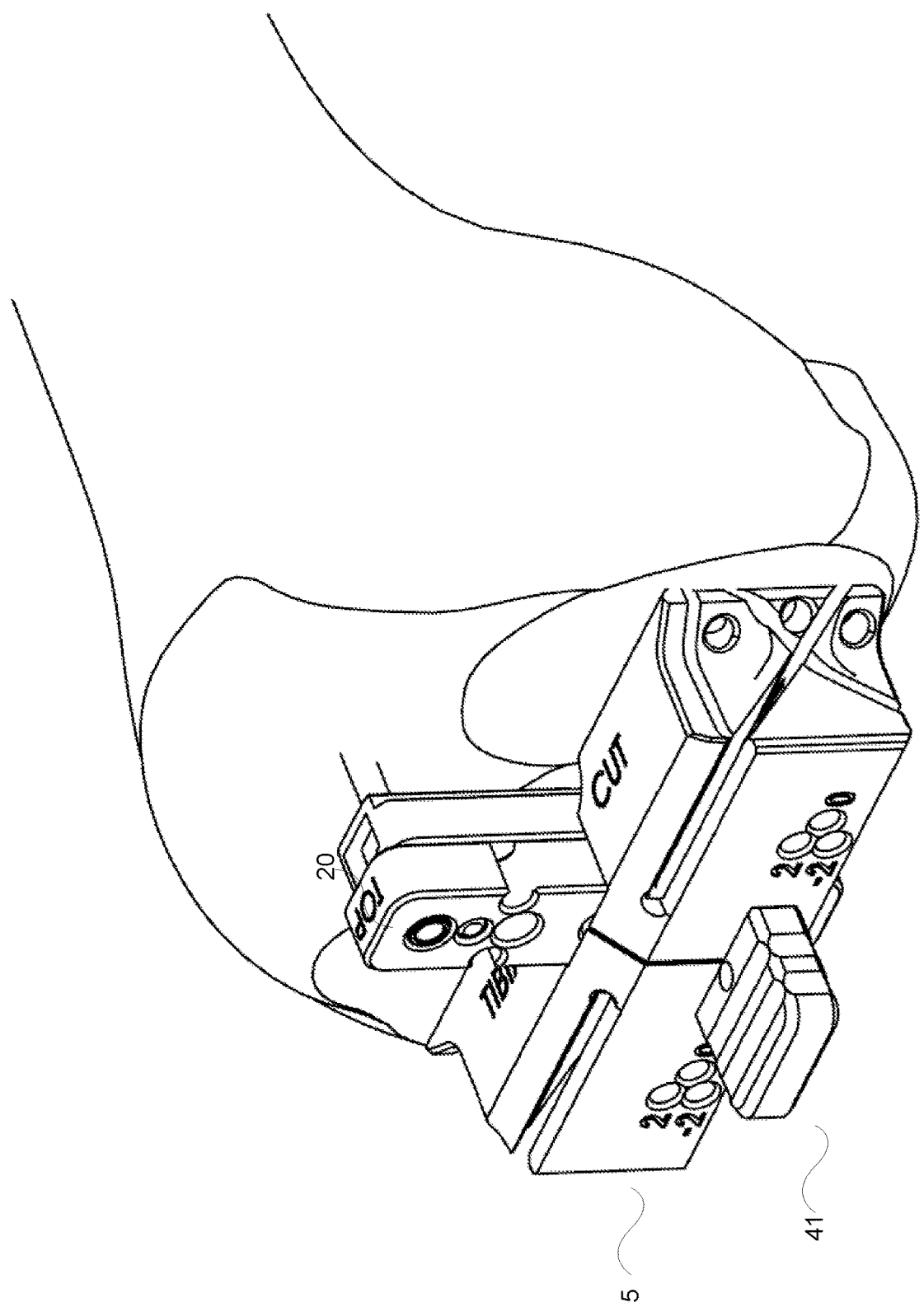

Turning now to FIG. 32, the cutting block guide 5 of matching size is placed over the punch card 20 wherein the locking tab 41 is utilised to locate the cutting block guide 5 with reference to the lowest holeset of the punch card 20.

Figure 33:
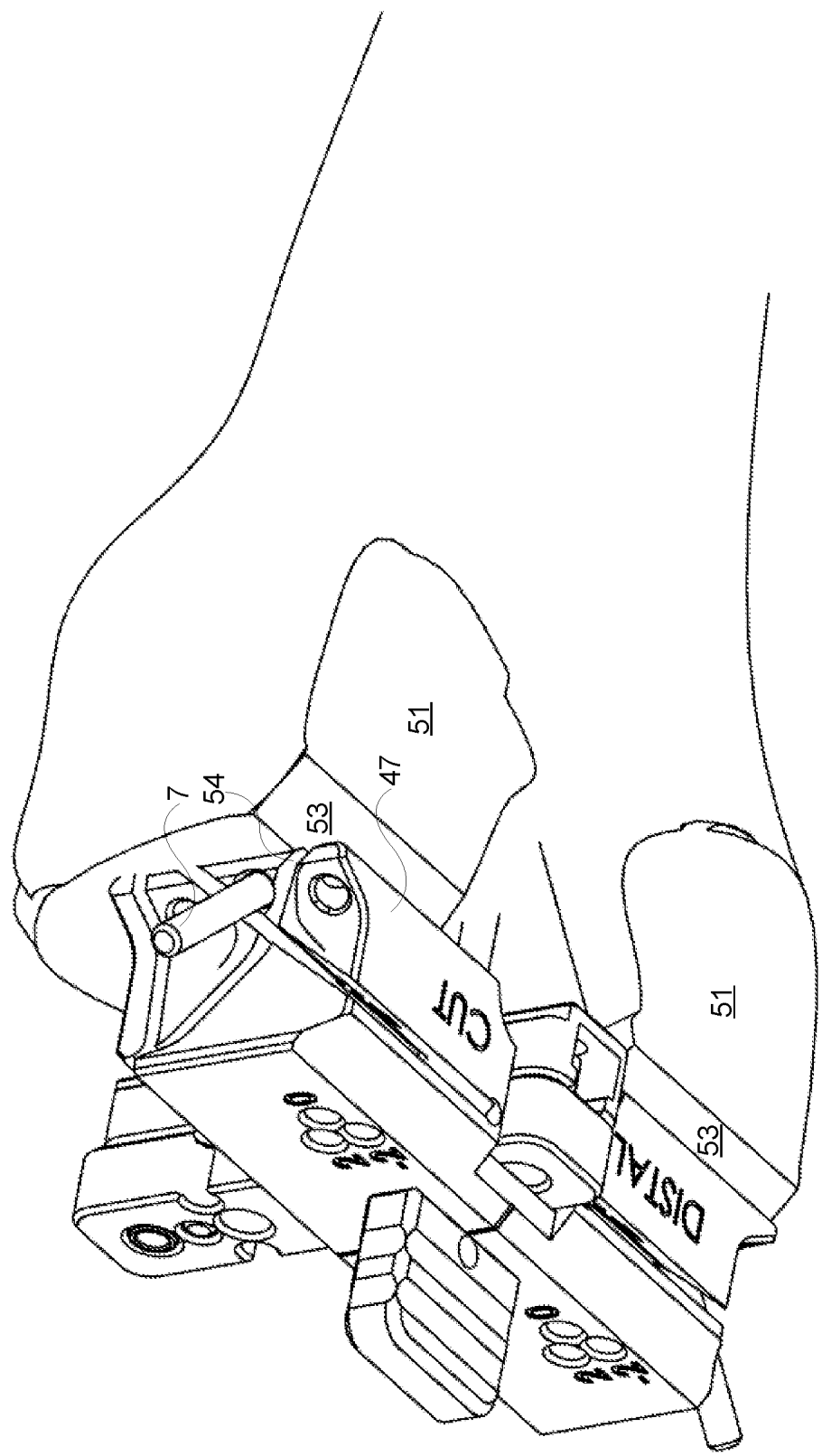

FIG. 33 shows the placement of fastening pins 7 to pin the cutting block guide 5 with reference to the lowest holeset for the making of the posterior and posterior chamfer resection. Specifically, the distal face 47 of the cutting block is utilised to make the posterior resection 51 and the posterior chamfer slot 54 is used to make the posterior chamfer resection 53.

Figure 34:
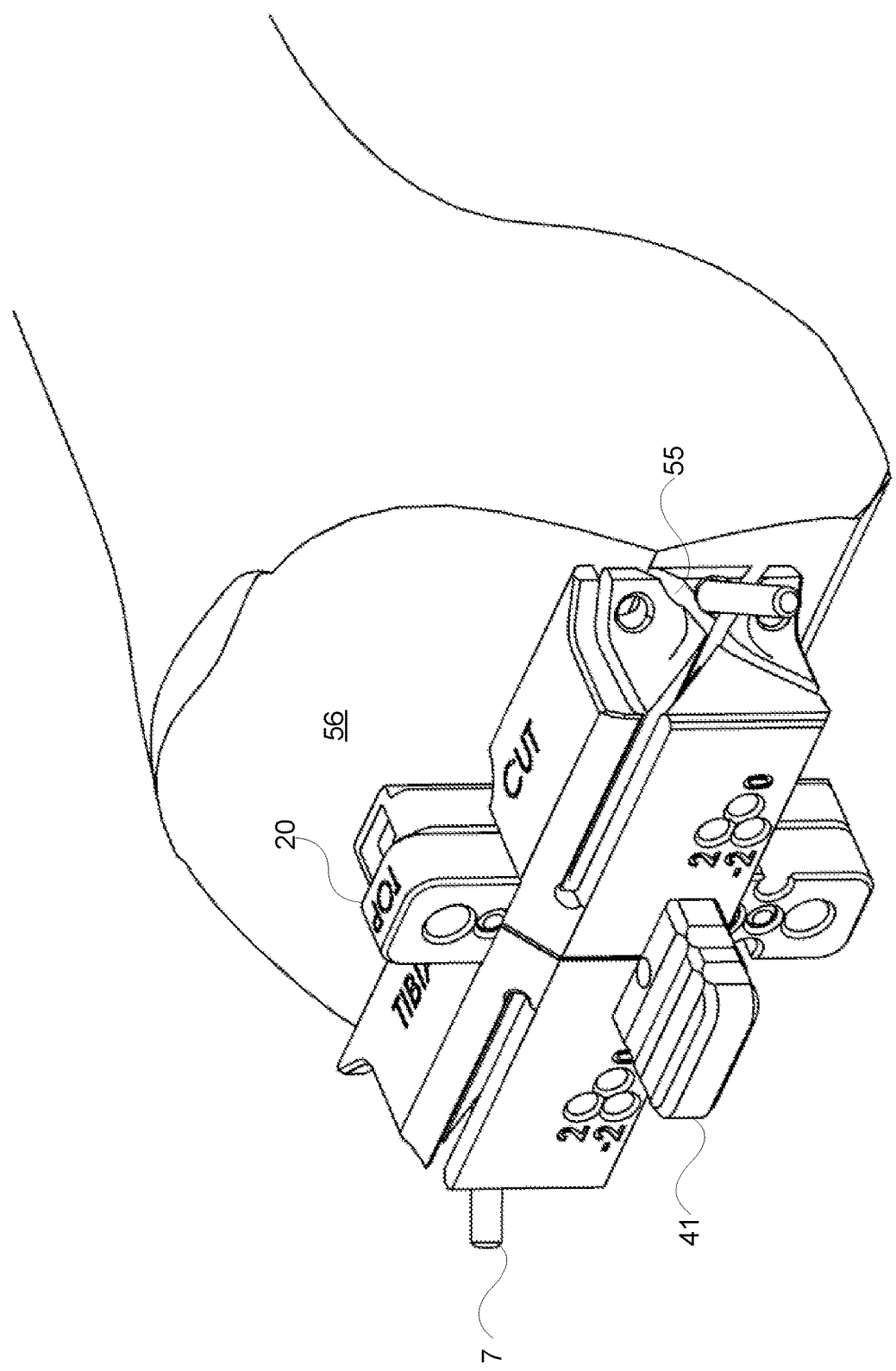

FIG. 34 shows the pulling of the locking tab 41 so as to allow the cutting block guide 5 to slide anteriorly along the punch card 22 locate to the middle holeset of the punch card 20 wherein the cutting block guide 5 is again pinned utilising fastening pins 7.

In this position, the anterior chamfer resection 56 is made utilising anterior chamfer slot 55.

Figure 35:
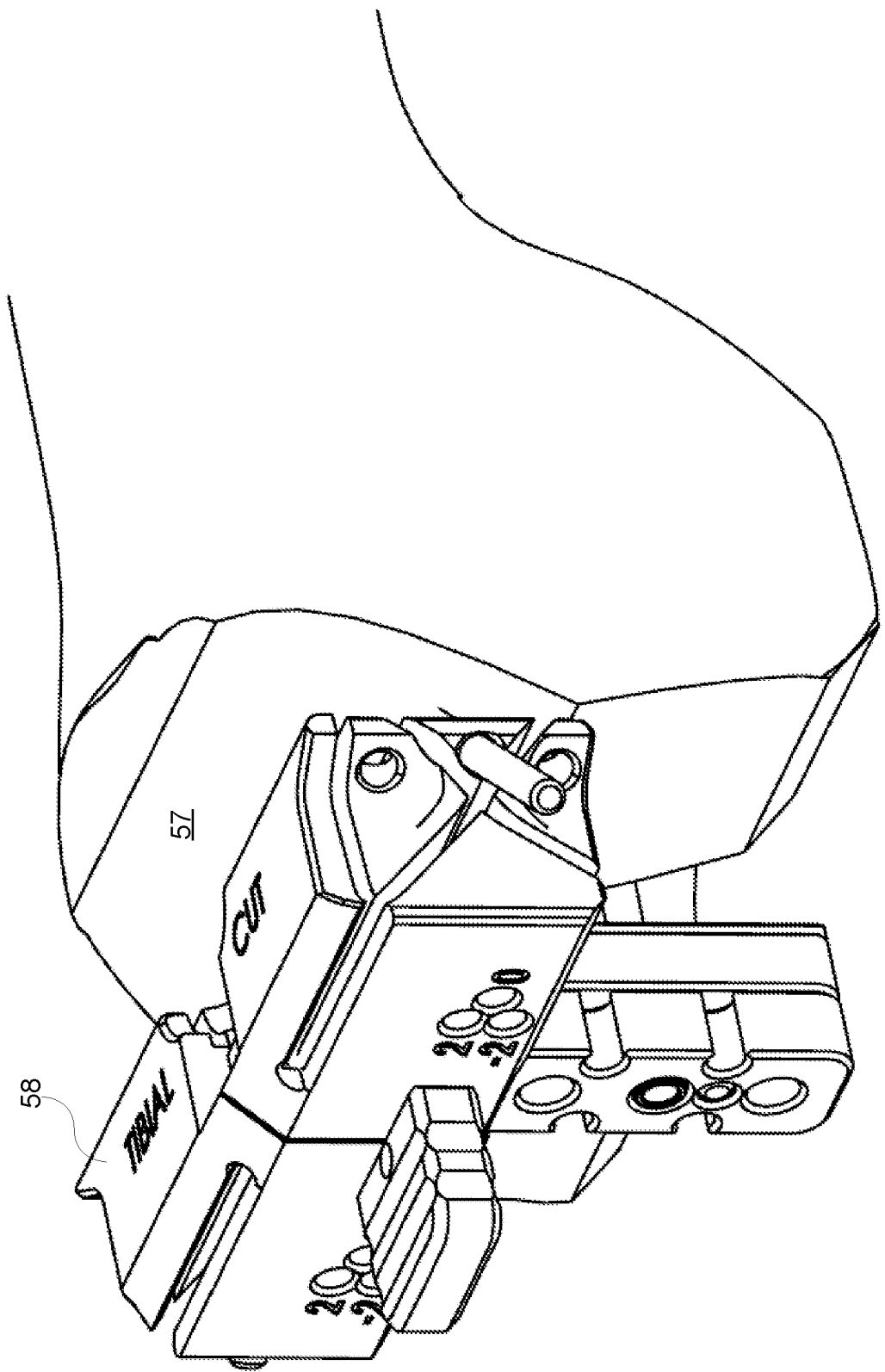

FIG. 35 shows the process being repeated wherein the cutting block guide 5 is slid further along the punch card 20 so as to locate at the top holeset so as to make the anterior resection 57 utilising the anterior face 58 of the cutting block guide 5.

It should be noted that if downsizing is required, the next smaller punch card 20 can be placed onto the placement pins 32 and the process repeated.

Figure 36:
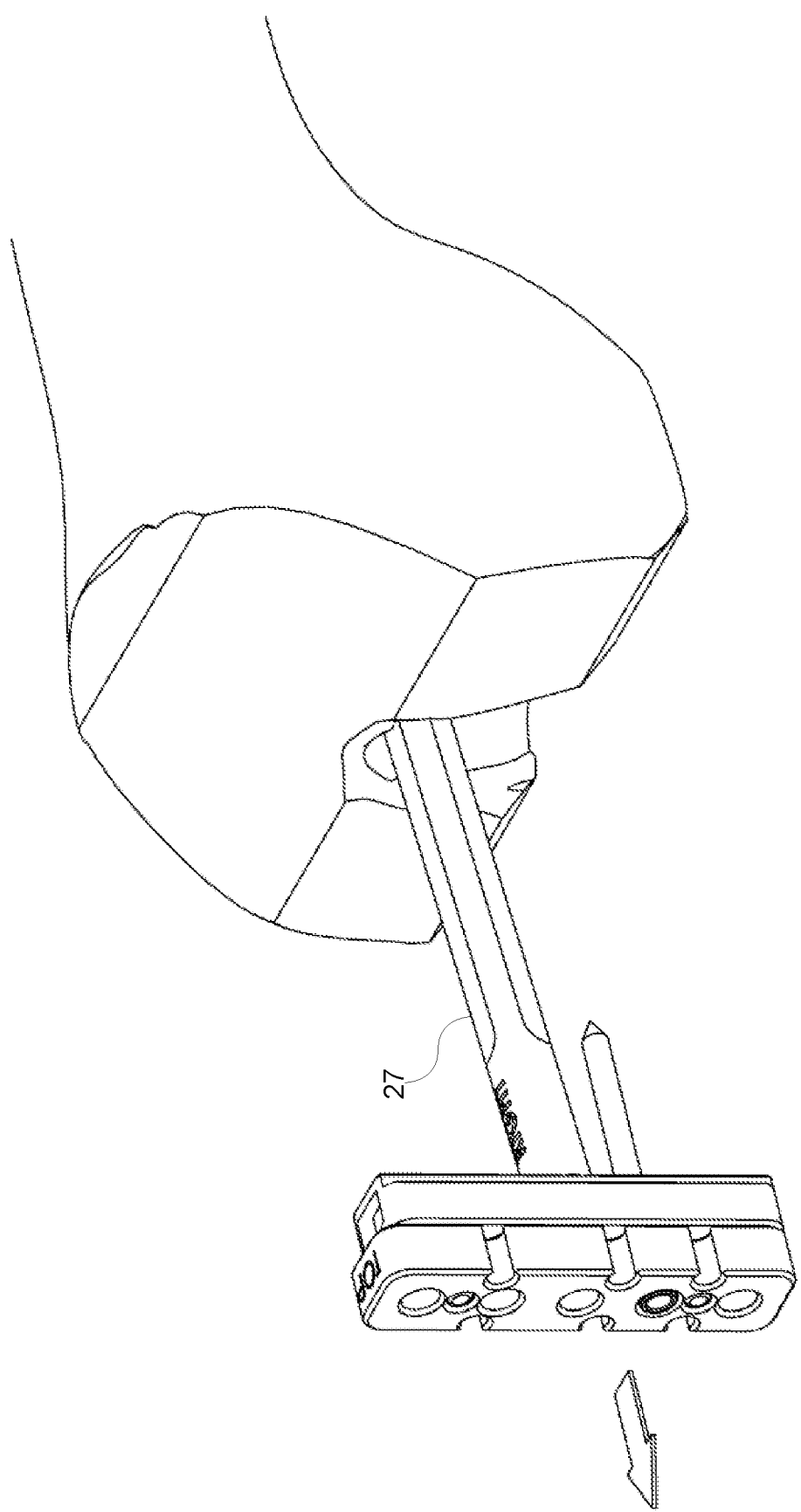

FIG. 36 shows the rod 27 being removed from the resected femur.

Figure 37B:
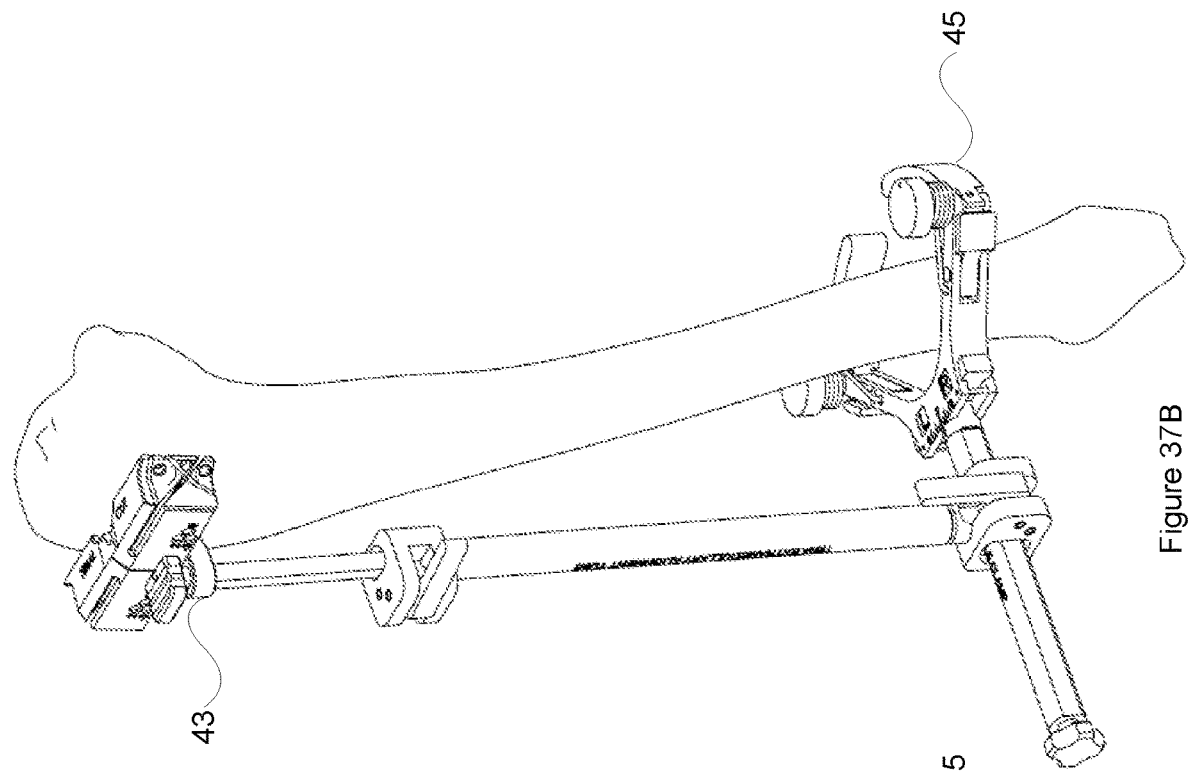
Figure 37A:
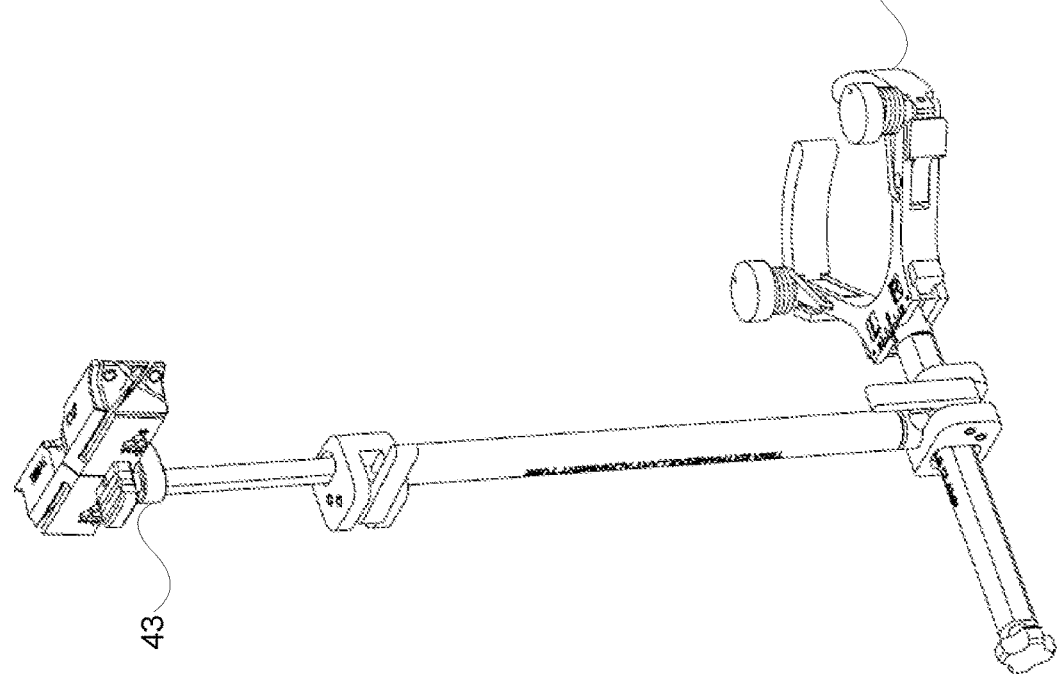

Turning now to FIG. 37, there is shown the making of the proximal tibial resection wherein the cutting block guide 5 is assembled to the tibial extramedullary rod 43 which is telescopic so as to allow the correct positioning of the cutting block guide 5 which can then be pinned for the making of the distal resection. Alternatively, the tibial intermedullary guide 42 may be utilised in conjunction with an intermedullary tibial rod 27.

Returning to FIG. 14, the various faces of the cutting block guide 5 are considered again in further detail. Specifically, and for orientation referencing convenience, there is shown the cutting block guide 5 comprising a top face 61, a bottom face 62, a posterior face 59 and anterior face 60.

As alluded to above, the posterior face 59 is utilised for making the distal femoral resection when the posterior face 59 is orientated substantially orthogonal to the elongate axis of the femur.

Then, the cutting block guide 5 is configured such that top face 61 is for making the proximal tibial resection when the top face is orientated substantially orthogonal to the elongate axis of the tibia in use.

The cutting block guide 5 is further configured such that the anterior face 60 is for making the anterior femoral resection and the posterior face 59 is used for making the posterior femoral resection.

The cutting block guide 5 comprises the posterior chamfer slot 54 used for making the posterior chamfer resection and the anterior chamfer slot 55 used for making the anterior chamfer resection.

As described above, cutting block guide 5 is configured for making two or more of the anterior femoral, posterior femoral, posterior chamfer femoral and anterior chamfer femoral resections when the cutting block guide is in two or more positions along an orthogonal axis substantially orthogonal to an elongate axis of a femur being resected in use.

Preferably, the posterior and posterior chamfer resections are made when the cutting block guide 5 is in a first position on the punch card 20 with reference to the femur along the orthogonal axis, the anterior chamfer resection is made when the cutting block guide is in a second position on the punch card 20 with reference to the femur along the orthogonal axis and the anterior resection is made when the cutting block guide 5 is in a third position on the punch card 20 with reference to the femur along the orthogonal axis.

In alternative embodiments, the cutting block guide 5 may be configured such that the various resections are made at other positions within the purposive scope of the embodiments described herein.

Interpretation

EMBODIMENTS

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

COMPRISING AND INCLUDING

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

SCOPE OF INVENTION

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to the orthopaedic industries.

The invention claimed is:

1. Intramedullary based and omni-positionable cutting guide instrumentation for femoral epiphysis resection for knee prosthesis placement comprising:
   an intramedullary placement guide configured for insertion into a medullary cavity of a femoral epiphysis in use, the placement guide having an anterior/posterior adjustment mechanism;
   a posterior referencing sizing jig for fastening to the anterior/posterior adjustment mechanism, the posterior rotational referencing sizing jig configured for referencing anterior and posterior surfaces of the femoral epiphysis so as to adjust the anterior/posterior offset of the anterior/posterior adjustment mechanism in use; and
   a punch card for subsequent fastening to the anterior/posterior adjustment mechanism, the punch card comprising a plurality of position referencing apertures for receipt of at least one locking pin of a cutting block guide therein for the purposes of allowing the anterior/posterior positioning of the cutting block guide at a first position for the purposes of making a first resection and at a second position for the purposes of making a second resection.

2. Cutting guide instrumentation as claimed in claim 1, wherein the plurality of apertures comprises an aperture located for locating the cutting block guide for the purposes of making a posterior resection.

3. Cutting guide instrumentation as claimed in claim 2, further comprising the cutting block guide and wherein the cutting block guide comprises a posterior face configured for guiding the posterior resection.

4. Cutting guide instrumentation as claimed in claim 1, wherein the plurality of apertures comprises an aperture located for locating the cutting block guide for the purposes of making a posterior chamfer resection.

5. Cutting guide instrumentation as claimed in claim 4, further comprising the cutting block guide and wherein the cutting block guide comprises a posterior chamfer slot configured for guiding the posterior resection.

6. Cutting guide instrumentation as claimed in claim 5, wherein the chamfer slot is bifurcated in comprising respective lateral/medial accessible slot portions.

7. Cutting guide instrumentation as claimed in claim 1, wherein the plurality of apertures comprises an aperture located for locating the cutting block guide for the purposes of making an anterior resection.

8. Cutting guide instrumentation as claimed in claim 7, further comprising the cutting block guide and wherein the cutting block guide comprises an anterior face configured for guiding the anterior resection.

9. Cutting guide instrumentation as claimed in claim 8, further comprising the cutting block guide and wherein the cutting block guide comprises a chamfer slot configured for guiding the posterior resection.

10. Cutting guide instrumentation as claimed in claim 9, wherein the chamfer slot is bifurcated in comprising respective lateral/medial accessible slot portions.

11. Cutting guide instrumentation as claimed in claim 1, wherein the plurality of apertures comprises an aperture located for locating the cutting block guide for the purposes of making an anterior chamfer resection.

12. Cutting guide instrumentation as claimed in claim 1, wherein the anterior/posterior adjustment mechanism comprises a sliding member configured to travel along an anterior/posterior axis of the femoral epiphysis in use.

13. Cutting guide instrumentation as claimed in claim 12, wherein the sliding member comprises placement pins configured for engaging the sizing jig.

14. Cutting guide instrumentation as claimed in claim 1, wherein the posterior rotational referencing sizing jig comprises a size guide configured for estimating the sizing of the femoral epiphysis.

15. Cutting guide instrumentation as claimed in claim 1, wherein the posterior rotational referencing sizing jig is configure for selectively engaging the placement guide at an anterior reference position and a posterior reference position.

16. Cutting guide instrumentation as claimed in claim 1, wherein the posterior rotational referencing sizing jig comprises a spacer for internal rotation positioning the anterior/posterior adjustment mechanism.

17. Cutting guide instrumentation as claimed in claim 16, wherein the internal rotation is substantially 3°.

18. Cutting guide instrumentation as claimed in claim 16, wherein the posterior rotational referencing sizing jig is selectively positional for left knee and right knee application.

19. Cutting guide instrumentation as claimed in claim 1, wherein the placement guide comprises a rod for insertion into the medullary cavity and a distal substantially orthogonal placement guide portion fastened to the rod.

20. Cutting guide instrumentation as claimed in claim 19, wherein the rod is orientated at an offset from the perpendicular axis of the placement guide portion to accommodate femoral varus.

21. Cutting guide instrumentation as claimed in claim 20, wherein the varus is substantially 6°.

22. Cutting guide instrumentation as claimed in claim 1, further comprising a right angled bracket configured for selective engagement to the placement guide for the purposes of locating a cutting block guide for the purposes of making a distal resection.

23. Cutting guide instrumentation as claimed in claim 22, wherein the right angled comprises laterally projecting condylar contacting flanges configured to control the positioning of the cutting block guide at a particular superior offset along the superior/inferior axis.

24. Cutting guide instrumentation as claimed in claim 23, wherein the superior offset is approximately 9 mm.

25. Cutting guide instrumentation as claimed in claim 22, further comprising the cutting block guide and wherein the cutting block guide comprises a plurality of apertures for receiving bone fastening pins therethrough for fastening the cutting block guide to the with respect to the femoral epiphysis for allowing the removal of the right angled bracket.

26. Cutting guide instrumentation as claimed in claim 25, wherein the plurality of apertures are collocated for providing placement tolerance.

27. Cutting guide instrumentation as claimed in claim 26, wherein the placement tolerance is lateral/medial placement tolerance.

28. Cutting guide instrumentation as claimed in claim 26, wherein the placement tolerance is superior/inferior placement tolerance.

29. Cutting guide instrumentation as claimed in claim 26, wherein the placement tolerance is approximately 2 mm.

30. A method for femoral epiphysis using the cutting guide instrumentation as claimed in claim 1.

* * * * *